(12) United States Patent
Rodriguez et al.

(10) Patent No.: US 10,271,880 B2
(45) Date of Patent: Apr. 30, 2019

(54) SYSTEMS AND METHODS FOR ANISOTROPY RESTORING FEMOROPLASTY

(71) Applicant: Beth Israel Deaconess Medical Center, Boston, MA (US)

(72) Inventors: Edward Rodriguez, Medfield, MA (US); Ara Nazarian, Watertown, MA (US)

(73) Assignee: Beth Israel Deaconess Medical Center, Inc., Boston, MA (US)

(*) Notice: Subject to any disclaimer, the term of this patent is extended or adjusted under 35 U.S.C. 154(b) by 24 days.

(21) Appl. No.: 14/649,994

(22) PCT Filed: Dec. 5, 2013

(86) PCT No.: PCT/US2013/073384
§ 371 (c)(1),
(2) Date: Jun. 5, 2015

(87) PCT Pub. No.: WO2014/089337
PCT Pub. Date: Jun. 12, 2014

(65) Prior Publication Data
US 2015/0313651 A1    Nov. 5, 2015

Related U.S. Application Data

(60) Provisional application No. 61/733,764, filed on Dec. 5, 2012.

(51) Int. Cl.
*A61B 17/74* (2006.01)
*A61B 17/88* (2006.01)
*A61B 17/00* (2006.01)

(52) U.S. Cl.
CPC .......... *A61B 17/74* (2013.01); *A61B 17/8858* (2013.01); *A61B 2017/00867* (2013.01)

(58) Field of Classification Search
CPC ... A61B 17/742; A61B 17/744; A61B 17/746; A61B 17/7208; A61B 17/7258; A61B 17/7266
See application file for complete search history.

(56) References Cited

U.S. PATENT DOCUMENTS 4,227,518 A   10/1980  Aginsky
5,281,225 A    1/1994  Vicenzi
(Continued)

FOREIGN PATENT DOCUMENTS

AT        399649 B      6/1995
EP     0882431 A1 *   12/1998   ......... A61B 17/7208
(Continued)

OTHER PUBLICATIONS

Beckmann, J., et al. "Fracture prevention by femoroplasty-cement augmentation of the proximal femur." Journal of Orthopaedic Research 29.11 (Apr. 15, 2011): 1753-1758.
(Continued)

*Primary Examiner* — Julianna N Harvey
(74) *Attorney, Agent, or Firm* — McCarter & English, LLP; Thomas O. Hoover

(57) ABSTRACT

The apparatus, systems and methods disclosed herein generally relate to the surgical repair or alteration of bone. More particularly, certain of the disclosed apparatus, systems and methods of the present disclosure relate to the use of a directionally-reinforced composite material to emulate anisotropic structural characteristics of an original anatomic trabecular structure. The directionally-reinforced composite material may generally include a scaffold set in a composite matrix, wherein the scaffold determines the anisotropic structural characteristics of the materials. In some of the embodiments, a scaffold may include at least a first plurality
(Continued)

of struts which are generally aligned in a first direction and a second plurality of struts aligned in a second direction.

35 Claims, 20 Drawing Sheets

(56) References Cited

U.S. PATENT DOCUMENTS

| | | | |
|---|---|---|---|
| 6,261,289 B1 * | 7/2001 | Levy | A61B 17/7266 606/62 |
| 6,551,321 B1 * | 4/2003 | Burkinshaw | A61B 17/7275 606/62 |
| 6,554,833 B2 | 4/2003 | Levy et al. | |
| 6,783,530 B1 | 8/2004 | Levy | |
| 7,052,498 B2 | 5/2006 | Levy et al. | |
| 7,507,241 B2 | 3/2009 | Levy et al. | |
| 7,601,152 B2 | 10/2009 | Levy et al. | |
| 7,670,339 B2 | 3/2010 | Levy et al. | |
| 7,789,900 B2 | 9/2010 | Levy et al. | |
| 7,828,802 B2 | 11/2010 | Levy et al. | |
| 8,029,506 B2 | 10/2011 | Levy et al. | |
| 8,133,232 B2 | 3/2012 | Levy et al. | |
| 8,197,515 B2 | 6/2012 | Levy et al. | |
| 2003/0130660 A1 * | 7/2003 | Levy | A61B 17/7266 606/63 |
| 2007/0173834 A1 | 7/2007 | Thakkar | |
| 2007/0250062 A1 | 10/2007 | Ara Pinilla et al. | |
| 2008/0269742 A1 | 10/2008 | Levy et al. | |
| 2009/0005782 A1 * | 1/2009 | Chirico | A61B 17/1617 606/63 |
| 2009/0182336 A1 | 7/2009 | Brenzel et al. | |
| 2010/0016983 A1 | 1/2010 | Smit | |
| 2010/0023012 A1 * | 1/2010 | Voor | A61B 17/74 606/64 |
| 2010/0076503 A1 | 3/2010 | Beyar et al. | |
| 2010/0087821 A1 | 4/2010 | Trip et al. | |
| 2013/0090655 A1 * | 4/2013 | Tontz | A61B 17/7233 606/64 |

FOREIGN PATENT DOCUMENTS

| | | |
|---|---|---|
| FR | 2844701 A1 | 3/2004 |
| SU | 967478 A1 | 10/1982 |
| WO | 03007830 A1 | 1/2003 |
| WO | 2005070314 A1 | 8/2005 |
| WO | 2009146457 A1 | 12/2009 |
| WO | 2010105174 A1 | 9/2010 |

OTHER PUBLICATIONS

Otake, Yoshito, et al. "An image-guided femoroplasty system: development and initial cadaver studies." SPIE Medical Imaging. International Society for Optics and Photonics, Feb. 13, 2010.

Sutter, Edward G., Simon C. Mears, and Stephen M. Belkoff. "A biomechanical evaluation of femoroplasty under simulated fall conditions." Journal of orthopaedic trauma 24.2 (Feb. 2010): 95.

Van der Steenhoven, T. J., et al. "Augmentation with silicone stabilizes proximal femur fractures: an in vitro biomechanical study." Clinical Biomechanics 24.3 (Mar. 2009): 286-290.

* cited by examiner

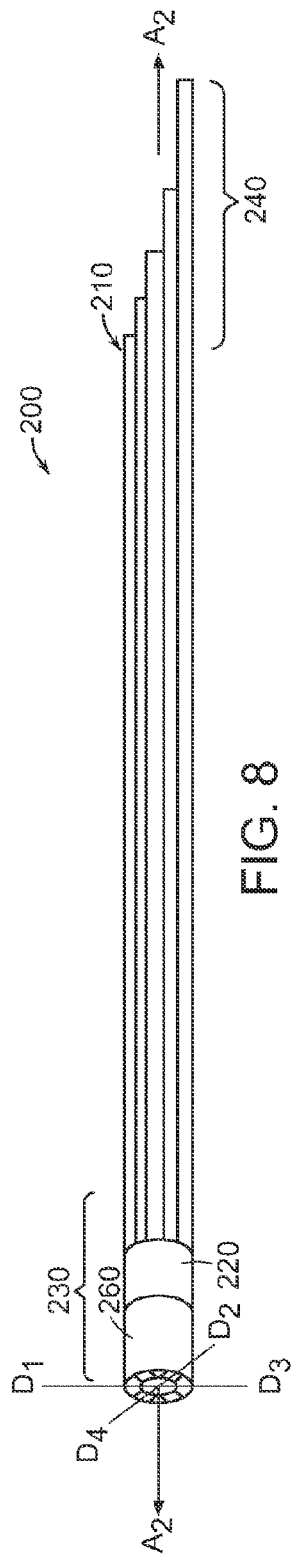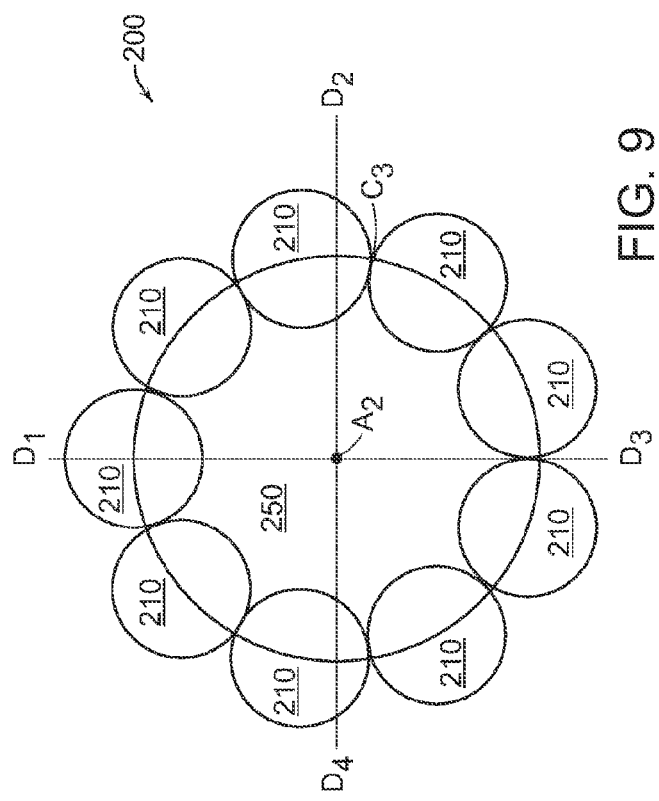
FIG. 8
FIG. 9

SYSTEMS AND METHODS FOR ANISOTROPY RESTORING FEMOROPLASTY

CROSS REFERENCE TO RELATED APPLICATIONS

The present application is a 35 U.S.C. § 371 national stage filing of International Application No. PCT/US2013/073384, filed on Dec. 5, 2013, which, in turn, claims priority to U.S. Provisional Application No. 61/733,764 filed on Dec. 5, 2012, the entire contents of both applications being incorporated herein by reference.

BACKGROUND OF THE INVENTION

Hip fractures present a serious and debilitating condition. Approximately 20-30% of hip fractures in geriatric patients result in death each year and many of the patients who survive will experience a significant loss of function. Hip fracture patients also experience medical and often cognitive co-morbidities making them highly vulnerable to post-operative decline and poor outcomes. Hip fractures have been recognized as the osteoporosis related fracture with the highest associated cost and morbidity.

The number of hip fractures occurring in the United States exceeded 300,000 in 2011, and hip fracture incidence is expected to increase with the aging population. Indeed, as people live longer, the number of hip fractures in the world, estimated at 1.7 million in 1990 is expected to rise exponentially to 6.3 million by the year 2050. By 2050, the worldwide incidence of hip fracture is projected to increase by 240% in women and 310% in men.

Following a hip fracture, patients are more likely to experience a fall, which is itself likely to generate considerable additional medical costs and to possibly result in a fracture in the uninjured hip. In 2000, the total direct medical costs of all fall injuries for people 65 and older exceeded $19 billion: $0.2 billion for fatal falls, and $19 billion for nonfatal falls. By 2020, the annual direct and indirect cost of fall injuries is expected to reach $54.9 billion (in 2007 dollars). In 2002, about 22% of community-dwelling seniors reported falling in the previous year. Medicare costs per fall averaged between $9,113 and $13,507. Among community-dwelling older adults, fall-related injury is one of the 20 most expensive medical conditions.

FIG. 1, demonstrates how osteoporosis results in thinning and loss of trabeculae, with a net effect of loss of bone mass and volume fraction (BV/TV), loss of connectivity and increased slenderness ratio (l/r), with concomittant facilitation of failure of individual trabecular elements. Once osteoclasts have resorbed enough bone tissue to create a discontinuity in a trabecular element, that element can no longer support load. As the cross-struts between longitudinally oriented trabeculae become discontinuous, the remaining trabeculae become relatively longer. Since buckling and bending are the predominant modes of trabecular deformation and failure, these changes in the trabecular structure influence the mechanical behavior of cancellous bone in disproportion to the corresponding change in mineral mass. The buckling load for a trabecular column is proportional to $EA/(l/r)2$, where E is the modulus of elasticity of the bone tissue comprising the trabeculae, A is the cross-sectional area of the trabeculae and l/r, the slenderness ratio, is measured as the effective length to width ratio of the trabeculae.

One may seek to counteract the architecture deterioration by inserting a filler material in bulk into the proximal femur. This insertion will create a polymerized block of material that is predominantly isotropic in structural and material properties. FIG. 2 illustrates the insertion of an isotropic elastomeric compound into the proximal femur. Unfortunately, this isotropic character does not mirror the directional, anisotropic behavior characterized by the healthy trabecular architecture of the proximal femur. Anisotropic materials have increased resistance along certain directions, such as bone along the trabecular architecture of the proximal femur, or wood along its grain direction. Isotropic materials fail predominantly by shearing forces, while anisotropic materials can be made to be significantly more resistant to failure along a preferred material direction.

Accordingly, there exists a need for interventional apparatus, systems and methods which reduce hip fracture risk. Particularly, there exists a need for apparatus, systems and methods which provide adequate anisotropic structural support.

SUMMARY OF THE INVENTION

The present invention relates to devices, systems and methods for improving the structural integrity of skeletal elements in human and animal bodies which can degrade over time due to injury disease or deterioration due to age. Exemplary embodiments specifically relate to the treatment of hip fractures or the preventative treatment of the femur, for example, due to the increased risk associated with osteoporosis. Consequently, the present invention provides for devices, systems and methods for improving the structural integrity at least a portion of a bone, for example, a femur bone, by inserting a first plurality of struts into the bone along a first axis, expanding the first plurality of struts substantially radially about the first axis to establish directional anisotropy along the first axis within the bone; and injecting a filler material about at least a portion of the first plurality of struts.

In exemplary embodiments, the first plurality of struts my each have a substantially same length. In further embodiments, the first plurality of struts have different lengths from one another.

In exemplary embodiments, the first plurality of struts may adapted for insertion into a femur bone at a location substantially opposite a femoral head of the femur bone, such that the first axis substantially passes into the femoral head. Thus, in some embodiments, at least some of the first plurality of struts may pass through the femoral neck and enter the femoral head. In exemplary embodiments, the expanding the first plurality of struts substantially radially about the first axis may cause the first plurality of struts to fan radially from the first axis at a distal end of the first plurality of struts such that the termination of the distal end of the struts is around the equatorial femoral head.

In yet further embodiments, the first plurality of struts may be adapted for insertion into a greater trochanter of a femur bone, for example, wherein the first axis extends generally from the greater trochanter to a lesser trochanter of the femur bone. Thus, in some embodiments, the expanding the first plurality of struts substantially radially about the first axis may cause a first set of one or more of the first plurality of struts are to be positioned cephally for termination at the lesser trochanteric and a second set of the one or more of the first plurality of struts to be positioned caudally for termination at the subtrochanteric area in the femoral canal, wherein the first set of struts is shorter than the second set of struts.

In exemplary embodiments, expanding the first plurality of struts substantially radially about the first axis may cause the first plurality of struts to fan out radially from the first axis at a distal end of the first plurality of struts. In some embodiments, the first plurality of struts may be fixed relative to one another at a proximal end thereof, for example in a circumferential arrangement. In some embodiments, the first plurality of struts may be configured to fan out radially in a circumferential arrangement.

Exemplary embodiments may further involve a guide element for at least one of (i) causing the struts to fan out radially from the central axis or (ii) determining a position at which the struts begins to fan out. In exemplary embodiments, the guide element may define a plurality of channels or paths for receiving and threading the first plurality of struts there through, whereby at least one of a relative positioning or curvature of each of the struts is determined. In some embodiments, the guide element may define alternative channels or paths for at least one of the struts in the first plurality of struts, for example, wherein the selecting between the alternative channels or paths is based on a physiology of the bone. The guide element may either remain fixed or be removed post implantation.

In exemplary embodiments, the guide element may be a wedge element for causing the first plurality of struts to fan out radially from the first axis. In some embodiments, the wedge element may be deployable from a collapsed state to a radially expanded state, for example, wherein the collapsed state of the wedge element enables insertion or removal thereof through a central channel defined by the first plurality of struts, and wherein the radially expanded state of the wedge element enables the first plurality of struts to fan out radially from the first axis, for example, when the axial position of the wedge element is adjusted along the first axis or as a function of the deployment of the wedge itself. In some embodiments, the wedge element may include a hinge mechanism which enables radial expansion of the wedge element when the wedge element is axially compressed along the first axis. In other embodiments, the wedge elements may define an expandable volume.

In exemplary embodiments, the guide element may be a sheath element for determining the position at which the struts begin to fan out. Thus, in some embodiments, adjusting the axial position the sheath element along the first axis may control the position at which the struts begin to fan out.

In exemplary embodiments, the first plurality of struts may be formed at least in part of shape-memory material having shape-memory, whereby the struts are configured to curve in a particular direction once the shape-memory of the shape-memory material is triggered. Thus, in some embodiments, the first plurality of struts may be self-expanding once inserted.

Exemplary embodiments may involve a second plurality of struts for insertion into the bone along a second axis different from the first axis. Similar to the first plurality of struts, the second plurality of struts may be expanded substantially radially about the second axis to establish directional anisotropy along the second axis within the bone and set in a filer material. In exemplary embodiments, the first and second pluralities of struts may crisscross to form an inter-linking scaffold. In some embodiments, the filler material may cross-link the first and second pluralities of struts.

In exemplary embodiments, the first plurality of struts may each have a substantially same length and at least two of the second plurality of struts may have different lengths from one another. In other embodiments, the first plurality of struts may be inserted into a femur bone at a location substantially opposite a femoral head of the femur bone, such that the first axis substantially passes through the femoral head and the second plurality of struts may be inserted into a greater trochanter of the femur bone. Thus, in some embodiments, the first plurality of struts pass through the femoral neck and enter the femoral head, for example, wherein the expanding the first plurality of struts substantially radially about the first axis may cause the first plurality of struts to fan radially from the first axis at a distal end of the first plurality of struts such that the termination of the distal end of the struts is around the equatorial femoral head. In further embodiments, the second axis may extends generally from the greater trochanter to a lesser trochanter of the femur bone, wherein the expanding the second plurality of struts substantially radially about the first axis may cause a first set of one or more of the second plurality of struts to be positioned cephally for termination at the lesser trochanteric and a second set of the one or more of the second plurality of struts to be positioned caudally for termination at the subtrochanteric area in the femoral canal, for example where the first set of struts is shorter than the second set of struts.

BRIEF DESCRIPTION OF THE DRAWINGS

FIG. 8 depicts a scaffold of certain embodiments in a collapsed position for use in forming a directionally-reinforced composite material.

FIG. 9 is cross-sectional perspective view of the scaffold of FIG. 8.

DETAILED DESCRIPTION OF THE INVENTION

Figure 1:
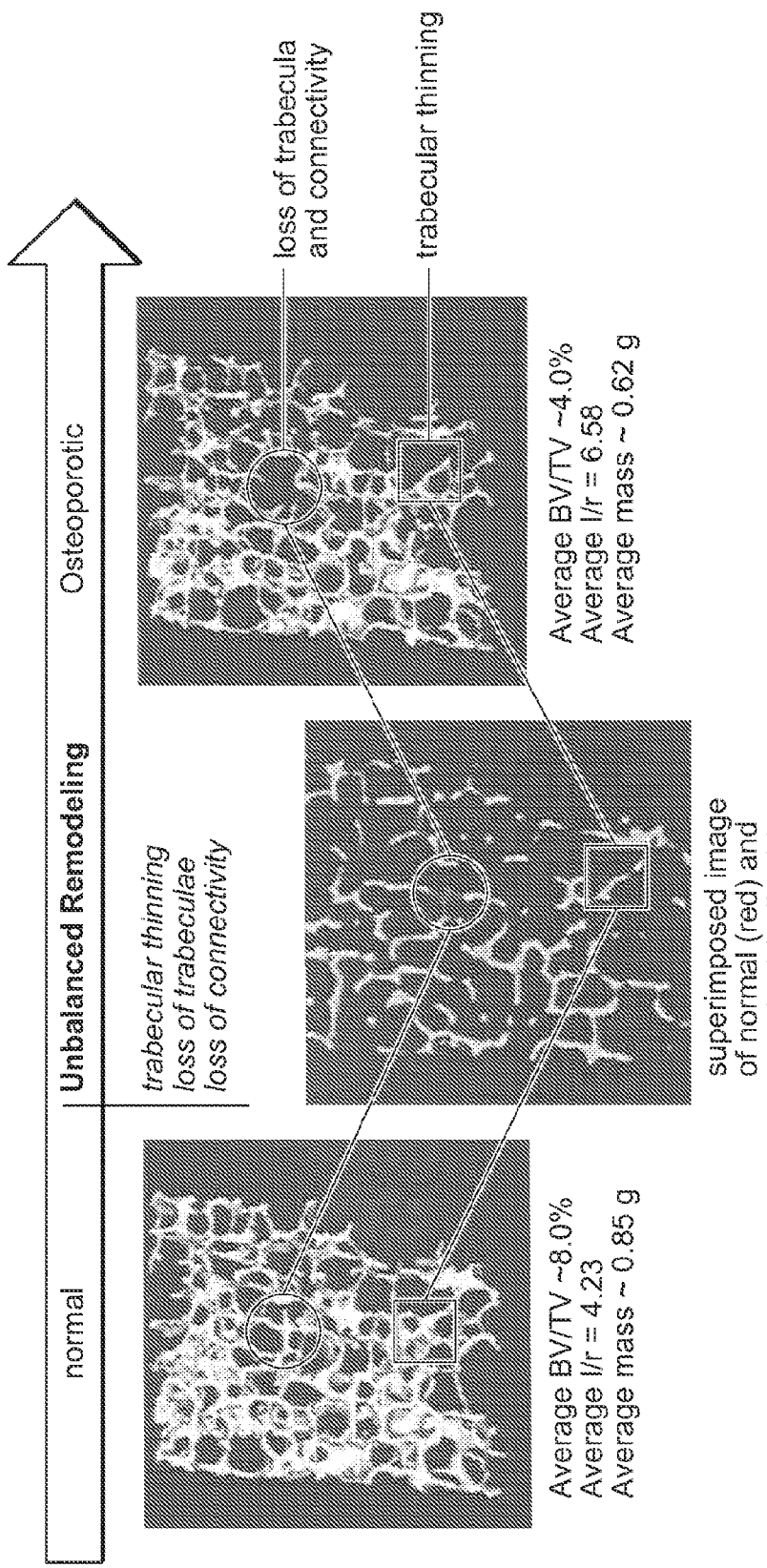
FIG. 1 depicts the deterioration of trabecular bone architecture with age and hormonal responses.
Figure 2:
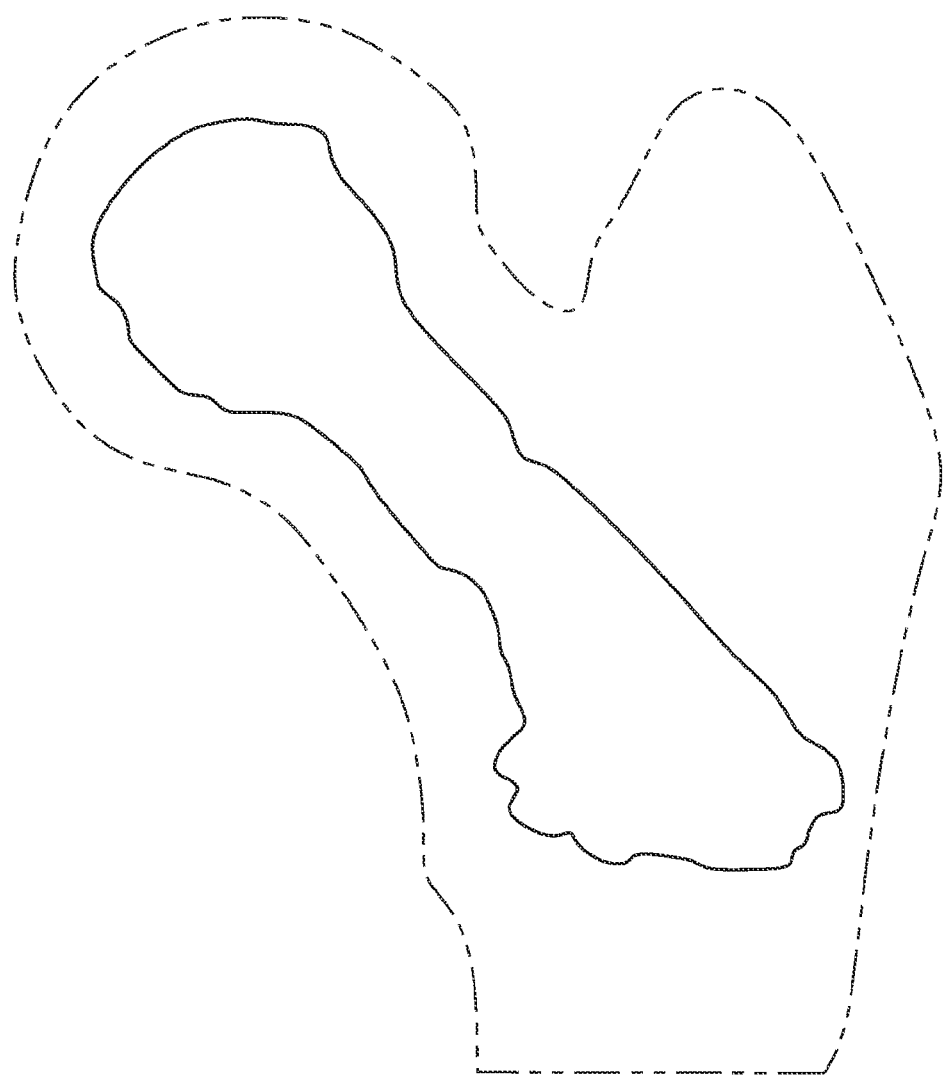
FIG. 2 illustrates the insertion of an isotropic elastomeric compound into the proximal femur

The apparatus, systems and methods disclosed herein generally relate to osteoplasty which is defined as surgical repair or alteration of bone. More particularly the disclosed apparatus, systems and methods of the present disclosure relate to the use of a directionally-reinforced composite material to emulate anisotropic structural characteristics of an original anatomic trabecular structure. The directionally-reinforced composite material may generally include a scaffold set in a composite matrix, wherein the scaffold determines the anisotropic structural characteristics of the materials. In general, a scaffold may include at least a first plurality of struts which, when deployed in the composite matrix, are generally aligned in a first direction thereby emulating the directional anisotropic behavior characterized by trabecular architecture of the proximal femur. Struts, as used herein may comprise without limitation any directionally specific structural member including, e.g., structural fibers, wires, cables, rods or other types of linear or arcuate structure constructed from stainless metals, titanium, nitinol, other metal alloys, non-metallic composites, ceramic materials, carbon fibers, carbon nanotubes, or combinations thereof.

In some embodiments, the plurality of struts may be deployed from a collapsed position to an expanded position before, during, or after implantation. The ability to deploy the struts from a collapsed to an expanded position may, for example, facilitate implantation via a single narrow entry point. The struts may then be expanded to provide structural reinforcement throughout the proximal femur. In exemplary embodiments, struts may be formed in part or wholly of a of a shape-memory alloy, shape memory-polymer or other shape-memory material, for example, to facilitate deployment thereof from a collapsed position to an expanded position. In other embodiments, the struts may be associated with one or more guide elements for guiding the struts into an expanded position and/or for determining a position at which the struts begins to fan out. For example, in some embodiments, the guide element may define a plurality of channels or paths for receiving and threading the struts therethrough, thereby defining a relative positioning and/or curvature of each of the struts. In further embodiments, the guide element may be configured to act as a wedge for causing the struts to fan out and/or sheath for determining a position at which the struts begin to fan out. The composite matrix may generally comprise a suitable bone filler material, e.g., PMMA, elastomeric polymer, Ca-Phosphate, or other existing or future bone substitute materials or combinations thereof, and may include absorbable or non-absorbable, osteogenic or non osteogenic, osteoinductive or non-osteoinductive, or osteoconductive or non osteoconductive materials, or combinations thereof. In exemplary embodiments, the composite material is formed in situ, by implanting the scaffold, deploying the scaffold to an expanded position, and finally injecting the composite matrix so that it sets around the deployed scaffold.

The apparatus, systems and methods disclosed herein are advantageous for patients at high risk for hip fracture secondary to osteoporosis. In particular, the apparatus, systems and methods disclosed enable high fracture and shear resistance from osteoplasties (beyond what has been presently described) utilizing a directionally-reinforced composite material. It is contemplated that the implantation and deployment of the apparatus and systems described herein may be routinely performed in an outpatient setting under local or spinal anesthetic in a minimally invasive manner, or performed as a preventive measure in the uninjured limb of a patient already presenting for surgical repair for a contralateral hip fracture.

Exemplary embodiments of the present disclosure relate to femoroplasty which is defined as surgical repair or alteration of the femur. More particularly, exemplary embodiments of the present disclosure relate to the use of a directionally-reinforced composite material to emulate anisotropic structural characteristics of the proximal femur, e.g., to repair an osteoporotic proximal femur. Thus, exemplary scaffolds are disclosed for implantation and deployment in the proximal femur.

More particularly, a femoral neck scaffold is disclosed for insertion along a femoral neck axis, which is defined as an axis extending generally through the femoral neck between the lateral cortex of the femur and femoral head (typically, approximately 135 degrees relative to the femoral shaft). The femoral neck scaffold may include a plurality of struts configured to fan out radially from the central axis at a distal end when deployed in an expanded position (e.g., such that the plurality of struts terminate at the equatorial femoral head at the distal end). The struts comprising the femoral neck scaffold are typically of approximately the same length to facilitate an even fanning out and termination of the distal ends of the struts around the equatorial femoral head. In exemplary embodiments, the struts may be fixed relative to one another at a proximal end of the scaffold, prior to the setting thereof in a composite matrix, for example, by a fixation element or a guide element associated with the proximal end. In other embodiments, the struts may only be fixed relative to one another by the setting thereof in the composite matrix.

Also disclosed is an intertrochanteric scaffold for insertion along an intertrochanteric axis, which is defined as an axis extending generally between the greater trochanter and the lesser trochanter of the femur. The intertrochanteric scaffold may include a plurality of struts configured to fan out radially from the central axis at a distal end when deployed in an expanded position (e.g., such that the plurality of struts terminate at the lesser trochanteric area in the femoral canal at the distal end). The struts comprising the intertrochanteric scaffold are typically variable in length to facilitate an even fanning out and termination of the distal ends of the struts at the lesser trochanteric area in the femoral canal. Thus, more cephalic struts are shorter for termination at the lesser trochanteric cortex while more caudal branches are longer for termination at the subtrochanteric area in the femoral canal. In exemplary embodiments, the struts may be fixed relative to one another at a proximal end of the scaffold, prior to the setting thereof in a composite matrix, for example, by a fixation element or a guide element associated with the proximal end. In other embodiments, the struts may only be fixed relative to one another by the setting thereof in the composite matrix.

In exemplary embodiments, a femoral neck scaffold and intertrochanteric scaffold may be used in conjunction with one another to form an inter-linking scaffold for the proximal femur. More particularly, the femoral neck scaffold and intertrochanteric scaffold may each be implanted and deployed resulting in a crisscrossing of the plurality of struts of the femoral neck scaffold with the plurality of struts of the intertrochanteric scaffold. The struts of the interlinking scaffold may then be cross-linked by injecting the composite matrix so that it sets around the deployed scaffold. Alternatively, the femoral neck scaffold and intertrochanteric scaffold may be used independently.

Although exemplary embodiments of the present disclosure relate to femoroplasty and in particular femoroplasty of the proximal femur, the apparatus, systems and methods disclosed are not limited to these embodiments. Rather, the apparatus, systems and methods disclosed may be applied with respect to any type of osteoplasty where the disclosed directionally-reinforced composite materials are configured to emulate anisotropic structural characteristics of an original anatomic trabecular structure. This novel approach of using directionally-reinforced composite materials for osteoplasty is particularly advantageous, resulting in increased strength and durability (e.g., the exemplary femoroplasty construct utilizing the interlinking scaffold resulted in increased resistance to femoral neck and intertrochanteric fractures exceeding peak energies sustained during falls from standing by 400%).

Insertion and deployment of certain embodiments of the proposed system can be conducted using a minimally invasive technique in an outpatient setting, with minimal surgical and anesthetic stress to the patient. Implantation can occur under spinal or general anesthesia as medically indicated in a surgical center or tertiary hospital. Indications for use will relate to the degree of osteoporosis and potential risk of fracture. A potential standard application in addition to the preventive planned insertion can be insertion of this fracture prevention device in the contralateral still unbroken hip at the time of repair of an already existing fracture in the other side.

At the time of insertion, incisions can be made on the lateral thigh not to exceed 2 cm each for insertion of both a retrograde anisotropy restoring femoropoasty (R-ARF) device (also referred to herein as a femoral neck scaffold) and an antegrade anisotropy restoring femoropoasty (A-ARF) device (also referred to herein as a intertrochanteric scaffold). Insertion can be made in a surgical or radiology suite under fluoroscopic imaging following standard angiography techniques. Drilling and insertion can be performed as described below, and patients can be discharged in full weight bearing status without restrictions and with minimal sutures to be removed at 2 weeks.

Figure 3:
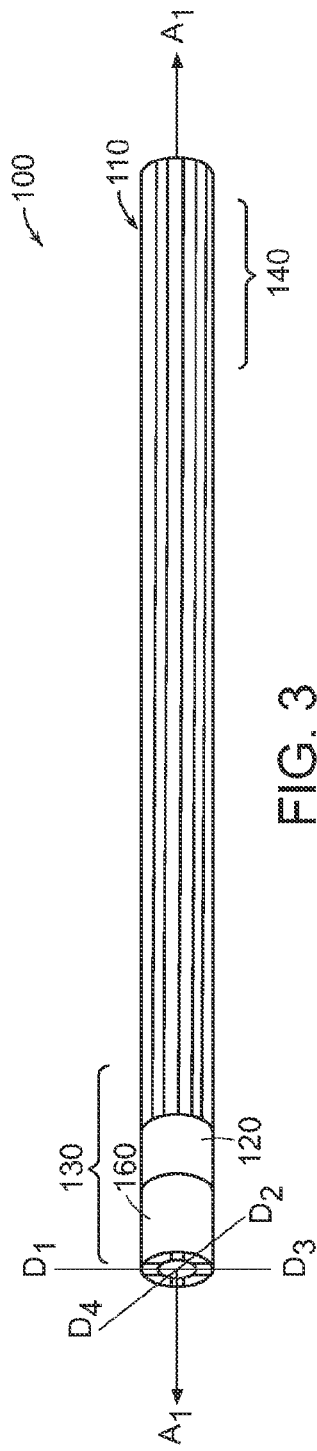
FIG. 3 depicts an exemplary scaffold of certain embodiments in a collapsed position for use in forming a directionally-reinforced composite material.
Figure 4:
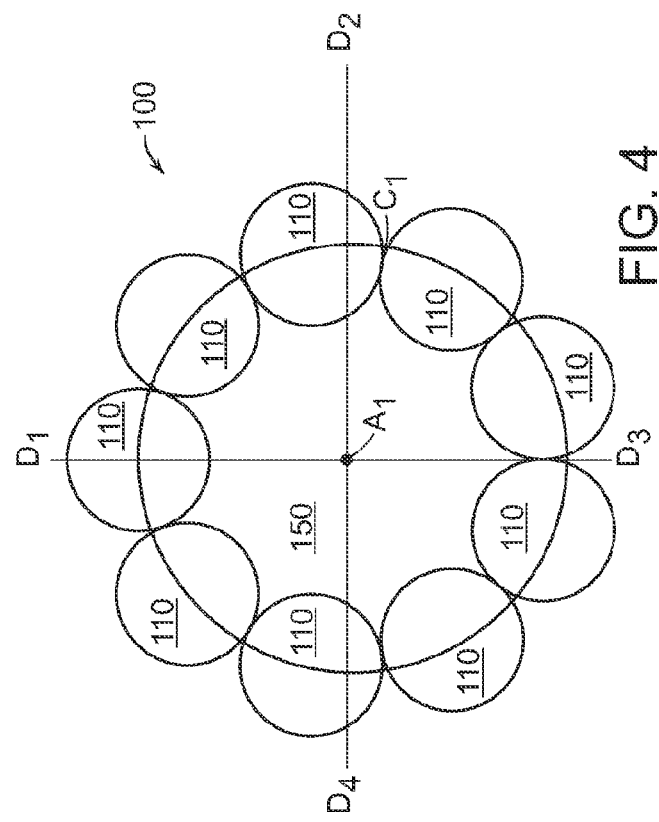
FIG. 4 is cross-sectional perspective of the scaffold of FIG. 3.
Figure 20:
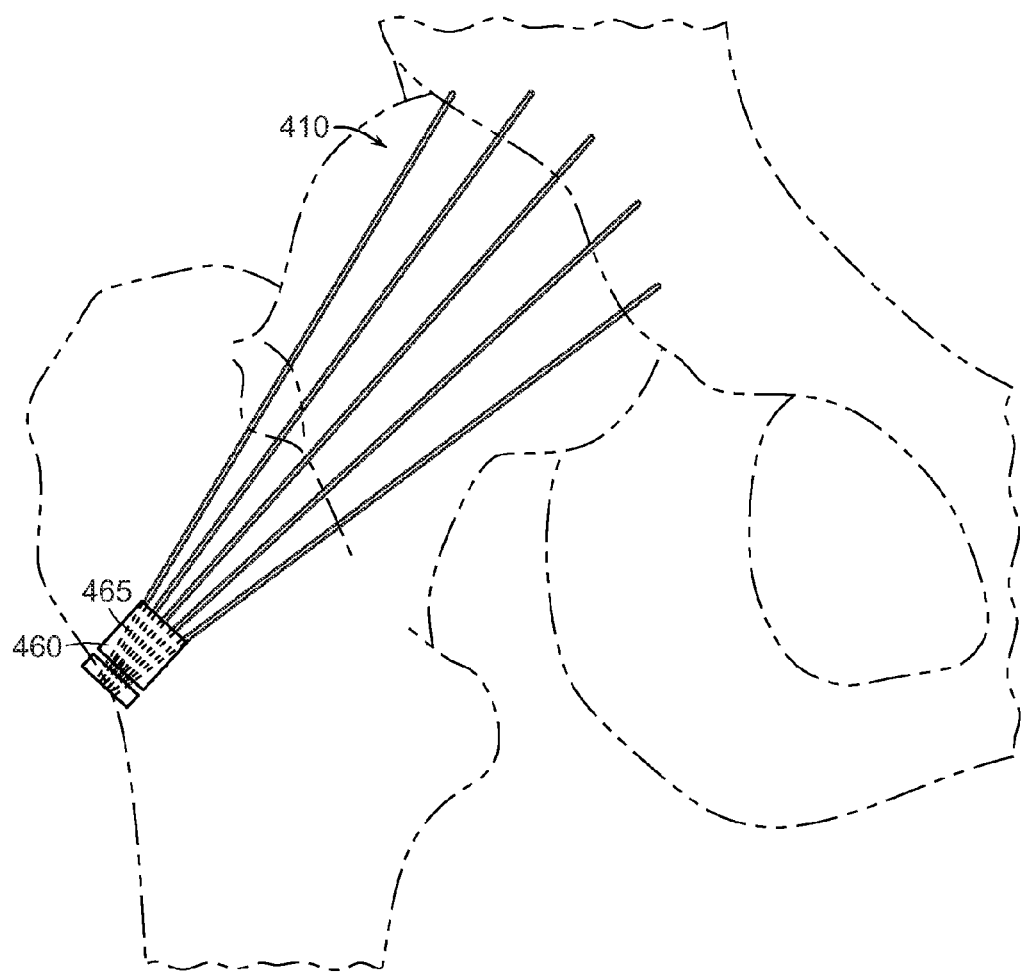
FIG. 20 depict further exemplary procedures and mechanisms for deploying certain of the expandable scaffolds of the present disclosure utilizing a guide element.
Figure 22:
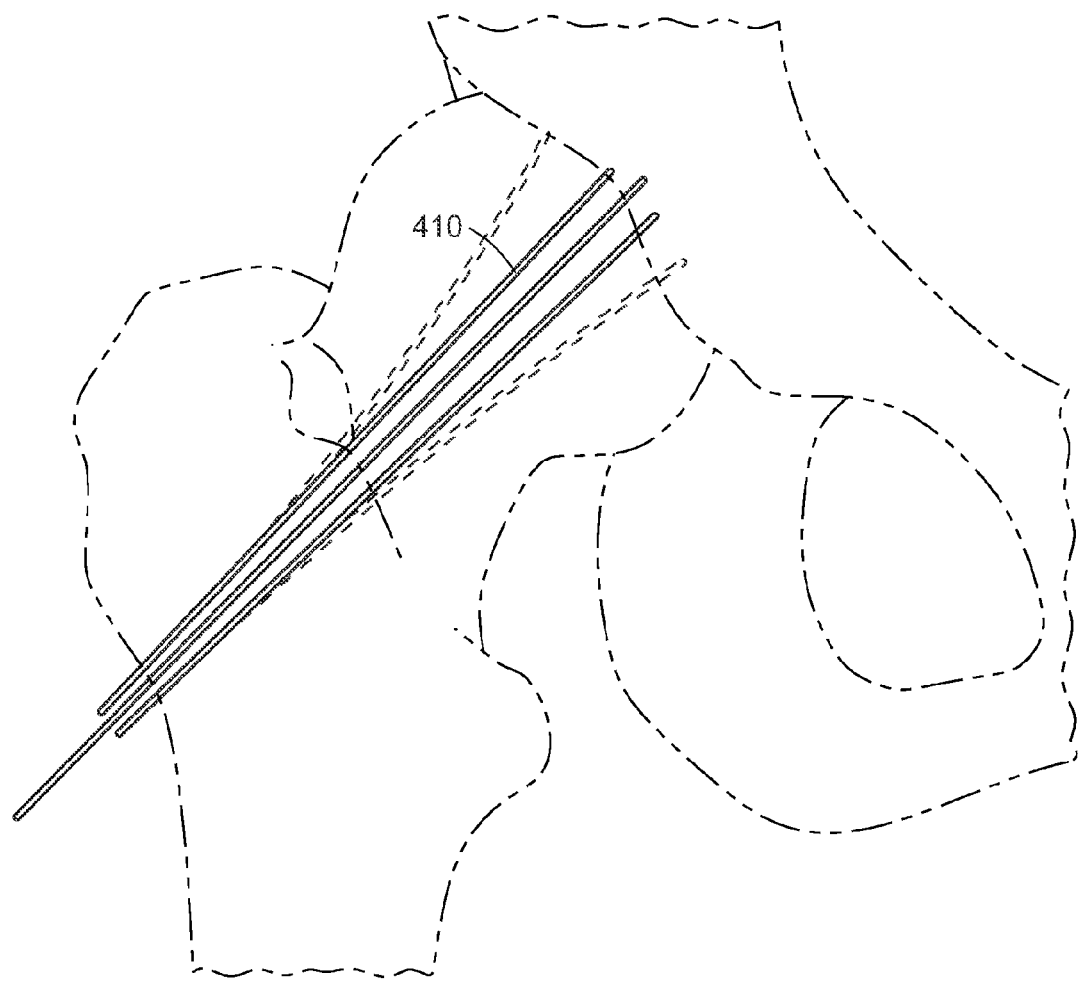
FIG. 22 depicts a further exemplary procedures and mechanisms for deploying certain of the expandable scaffolds of the present disclosure utilizing a shape-memory material.

With initial reference to FIGS. 3 and 4, an exemplary scaffold 100 for use in forming a directionally-reinforced composite material, as described herein, is depicted in a collapsed position. Exemplary scaffold 100 may be used as a femoral neck scaffold adapted for insertion along a femoral neck axis, e.g., wherein the resulting directionally-reinforced composite material (comprising the implanted and deployed scaffold 100 set in a composite matrix) is configured to emulate anisotropic structural characteristics of the anatomic trabecular structure of the femoral neck. Exemplary scaffold 100 generally includes a plurality of struts 110 which, in the collapsed position, may be aligned along a central axis A1 (also known as the insertion axis or implantation axis of the scaffold 100). As best depicted in FIG. 4, the plurality of struts 110 may be arranged circumferentially (C1) around the insertion axis A1 to define a central channel 150. In exemplary embodiments, the plurality of struts 110 may be fixed relative to one another at a proximal end 130, e.g., using a fixation element 120 such as a ring or band or other suitable attachment mechanism. In other exemplary embodiments (such as depicted in FIGS. 20 and 22), the plurality of struts 110 may only be fixed relative to one another post implantation, for example, by the setting thereof in a composite matrix. The scaffold 100 or individual struts 110 may also include one or more threaded portions, for example, threaded portion 160, at the proximal end for aiding in insertion and retrieval, e.g., using an insertion tool configured to cooperate with the threaded portions. Advantageously, the plurality of struts 110 are configured to fan out radially from the central axis A1 at the distal end 140 after deployment from the collapsed position to the expanded position, e.g., thereby emulating the anisotropic structural characteristics of the anatomic trabecular structure of the femoral neck. In exemplary embodiments, the struts 100 are of approximately the same length, e.g., to facilitate an even fanning out and termination of the distal ends of the struts around the equatorial femoral head after implantation and deployment. Thus, the struts 110 configured for positioning cephaly D1 caudally D3 anteriorly D2 and posteriorly D4 are all approximately the same length. In exemplary embodiments, the scaffold 100 is designed to be completely intraosseous, except for one or more threaded portions that allow for removal if needed. In exemplary embodiments (not depicted), scaffold 100 may include a circumferential arrangement of 11 cylindrical struts of 1.2 mm in diameter around a 3 mm diameter central channel. The overall diameter of the scaffold 100 may be 5 mm. The scaffold 100 or the individual struts 110 may be threaded over a 4.6 mm portion of the proximal end, e.g., for insertion and retrieval with an insertion tool.

Figure 5:
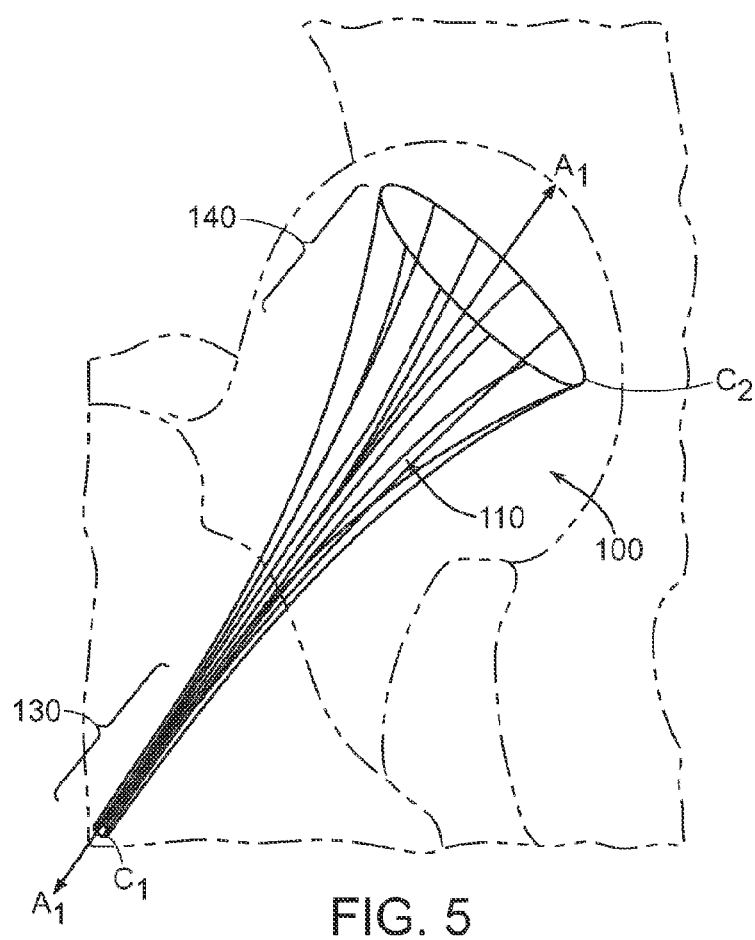
FIG. 5 depicts the implantation and deployment along the femoral neck axis of the scaffold of FIG. 3.
Figure 6:
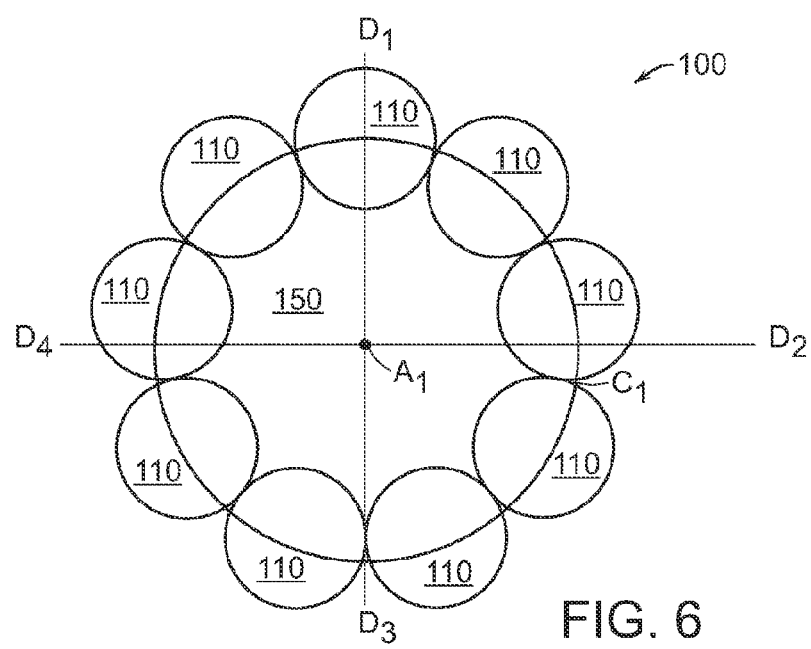
FIG. 6 is cross-sectional perspective of the scaffold of FIG. 3 during deployment in the closed position.
Figure 7:
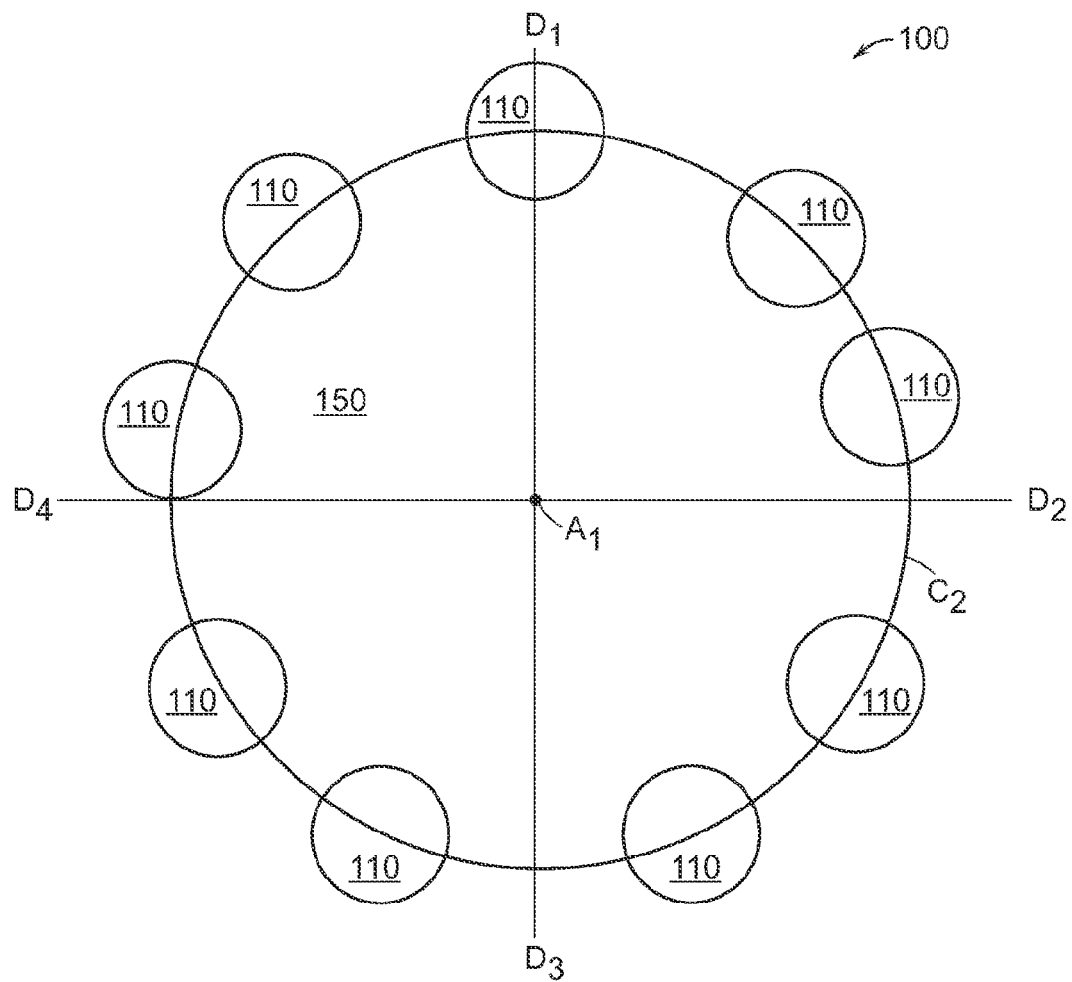
FIG. 7 is cross-sectional perspective of the scaffold of FIG. 3 during deployment in the open position.

FIGS. 5-7 depict the exemplary scaffold 100 after implantation and deployment along the femoral neck axis (which is aligned with the central axis A1 of the scaffold 100). As depicted, the plurality of struts 110 fan out radially (see C2) from the central axis A1 at the distal end 140 after deployment from the collapsed position to the expanded position. The distal ends of the struts 110 terminate around the equatorial femoral head (see C2) after implantation and deployment. In its expanded state, scaffold 100 emulates the anisotropic structural characteristics of the anatomic trabecular structure of the femoral neck. After implantation and deployment, scaffold 100 may be set in a composite matrix, e.g., by injecting the composite matrix into the central channel 150.

With reference to FIGS. 8 and 9, an further exemplary scaffold 200 for use in forming a directionally-reinforced composite material, as described herein, is depicted in a collapsed position. Exemplary scaffold 200 may be used as an intertrochanteric scaffold adapted for insertion along a intertrochanteric axis, e.g., wherein the resulting directionally-reinforced composite material (comprising the implanted and deployed scaffold 200 set in a composite matrix) is configured to emulate anisotropic structural characteristics of the anatomic trabecular structure of the femur along the intertrochanteric line. Exemplary scaffold 200 generally includes a plurality of struts 210 which, in the collapsed position, may be aligned along a central axis A2 (also known as the insertion axis or implantation axis of the scaffold 200). As best depicted in FIG. 9, the plurality of struts 210 may be arranged circumferentially (C3) around the insertion axis A2 to define a central channel 250. In exemplary embodiments, the plurality of struts 210 may be fixed relative to one another at a proximal end 230, e.g., using a fixation element 220 such as a ring or band or other suitable attachment mechanism. In other exemplary embodiments (such as depicted in FIGS. 20 and 22), the plurality of struts 210 may only be fixed relative to one another post implantation, for example, by the setting thereof in a composite matrix. The scaffold 200 or individual struts 210 may also include a one or more threaded portions, for example threaded portion 260, at the proximal end for aiding in insertion and retrieval, e.g., using an insertion tool configured to cooperate with the threaded portions. Advantageously, the plurality of struts 210 are configured to fan out radially from the central axis A2 at the distal end 240 after deployment from the collapsed position to the expanded position, e.g., thereby emulating the anisotropic structural characteristics of the anatomic trabecular structure of the femoral neck. In exemplary embodiments, the struts 200 are variable in length to facilitate an even fanning out and termination of the distal ends of the struts at the lesser trochanteric area in the femoral canal after implantation and deployment. Thus, the struts configured for positioning cephally D1 are shorter (for termination at the lesser trochanteric cortex) while the struts configured for positioning caudally D3 are longer (for termination at the subtrochanteric area in the femoral canal). In exemplary embodiments, the scaffold 200 is designed to be completely intraosseous, except for one or more threaded portions that allows for removal if needed. In exemplary embodiments (not depicted), scaffold 200 may include a circumferential arrangement of 8 cylindrical struts of 1.6 mm in diameter around a 3 mm diameter central channel. The overall diameter of the scaffold 200 may be 5 mm. The scaffold 200 or the individual struts may be threaded over a 4.6 mm portion of the proximal end, e.g., for insertion and retrieval with an insertion tool.

Figure 10:
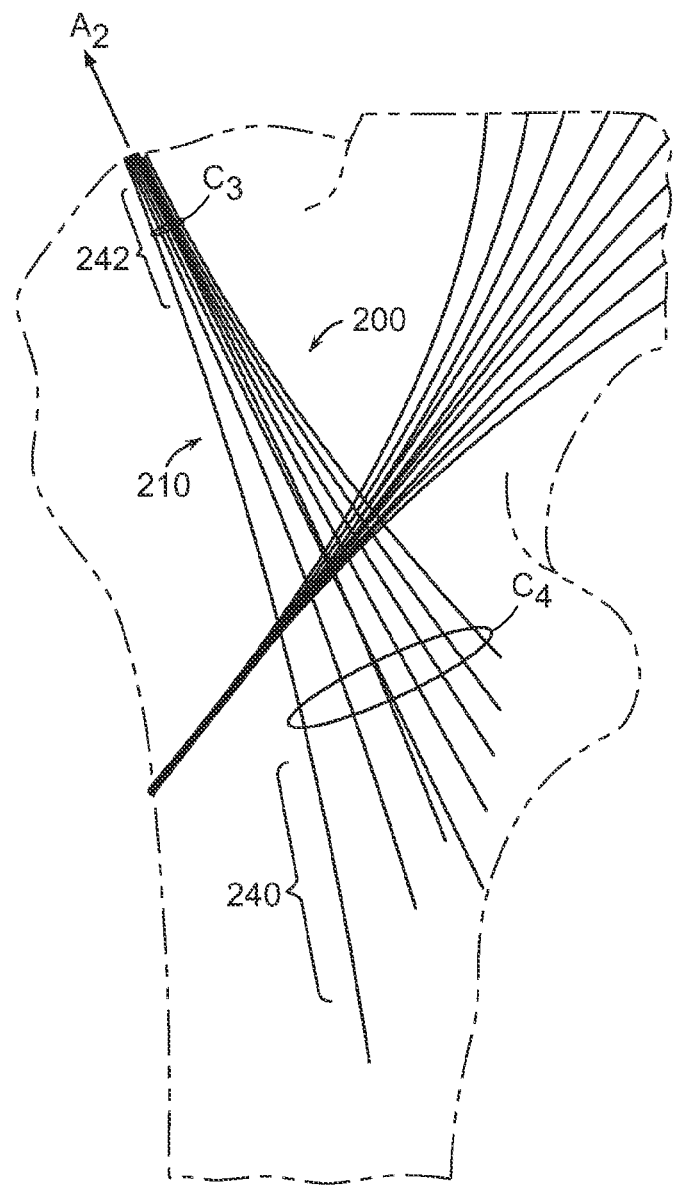
FIG. 10 depicts the exemplary scaffold of FIG. 8 after implantation and deployment along the femoral neck axis.
Figure 11:
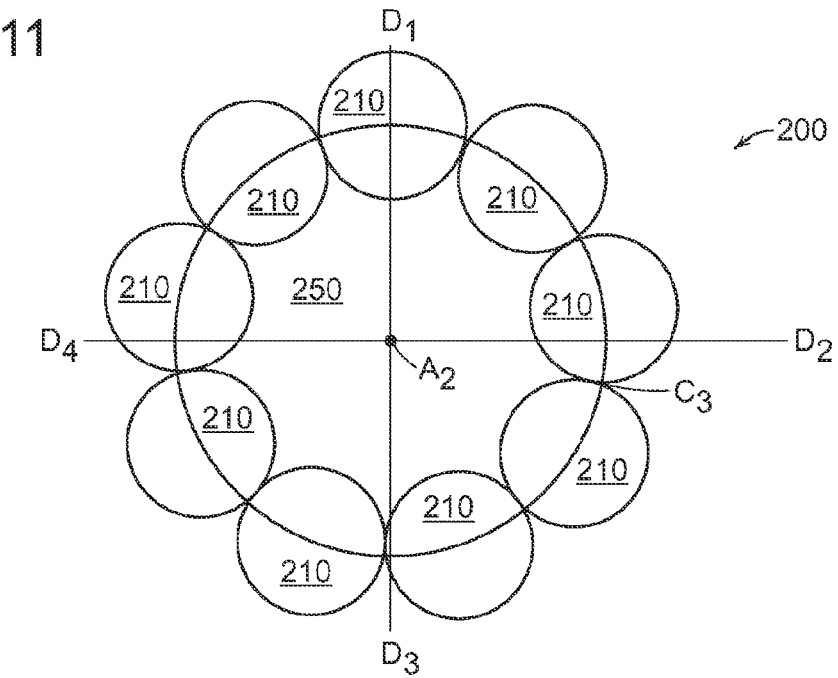
FIG. 11 is cross-sectional perspective of the scaffold of FIG. 8 during deployment in the closed position.
Figure 12:
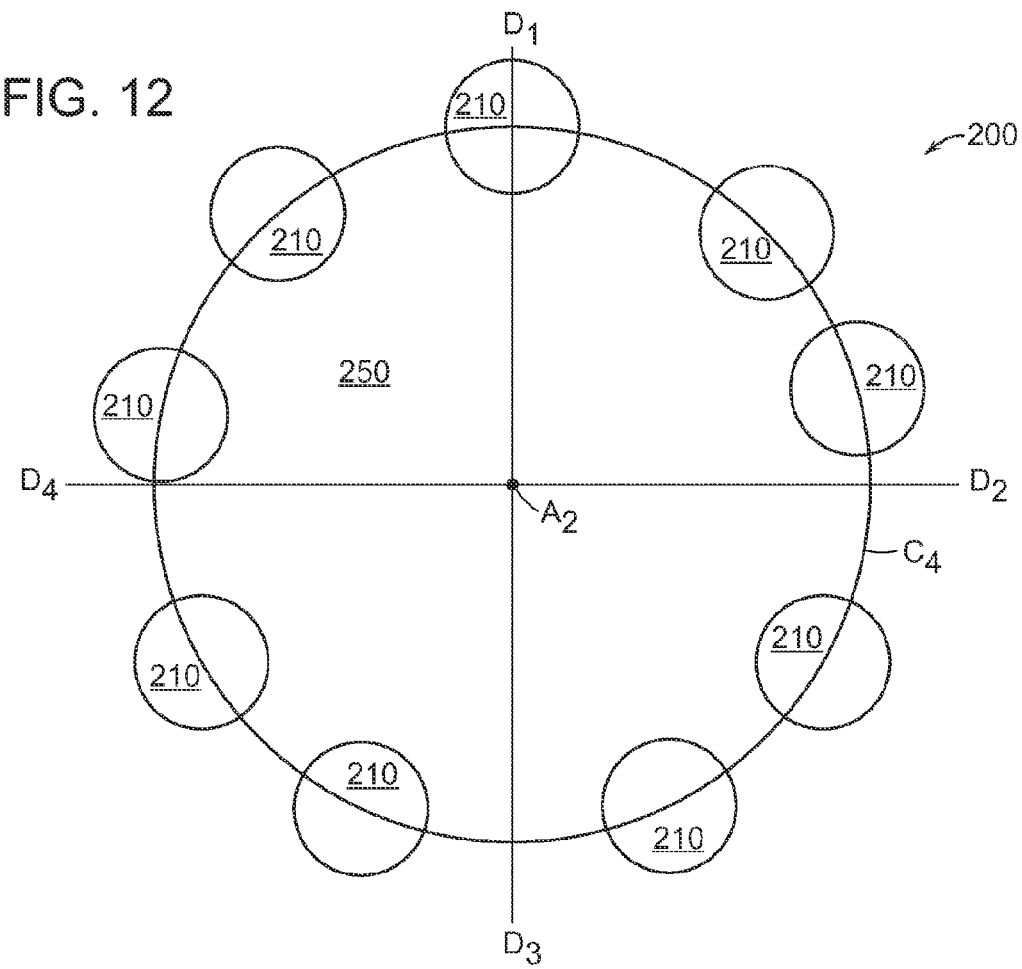
FIG. 12 is cross-sectional perspective of the scaffold of FIG. 8 during deployment in the open position.

FIGS. 10-12 depict the exemplary scaffold 200 after implantation and deployment along the femoral neck axis (which is aligned with the central axis A2 of the scaffold 200). As depicted, the plurality of struts 210 fan out radially (see C4) from the central axis A1 at the distal end 140 after deployment from the collapsed position to the expanded position. The distal ends of the struts 110 terminate around the lesser trochanteric cortex and subtrochanteric area in the medial femoral canal (see C4) after implantation and deployment. In its expanded state, scaffold 200 emulates the anisotropic structural characteristics of the anatomic trabecular structure of the femur along the intertrochanteric line. After implantation and deployment, scaffold 200 may be set in a composite matrix, e.g., by injecting the composite matrix into the central channel 250.

Figure 13A:
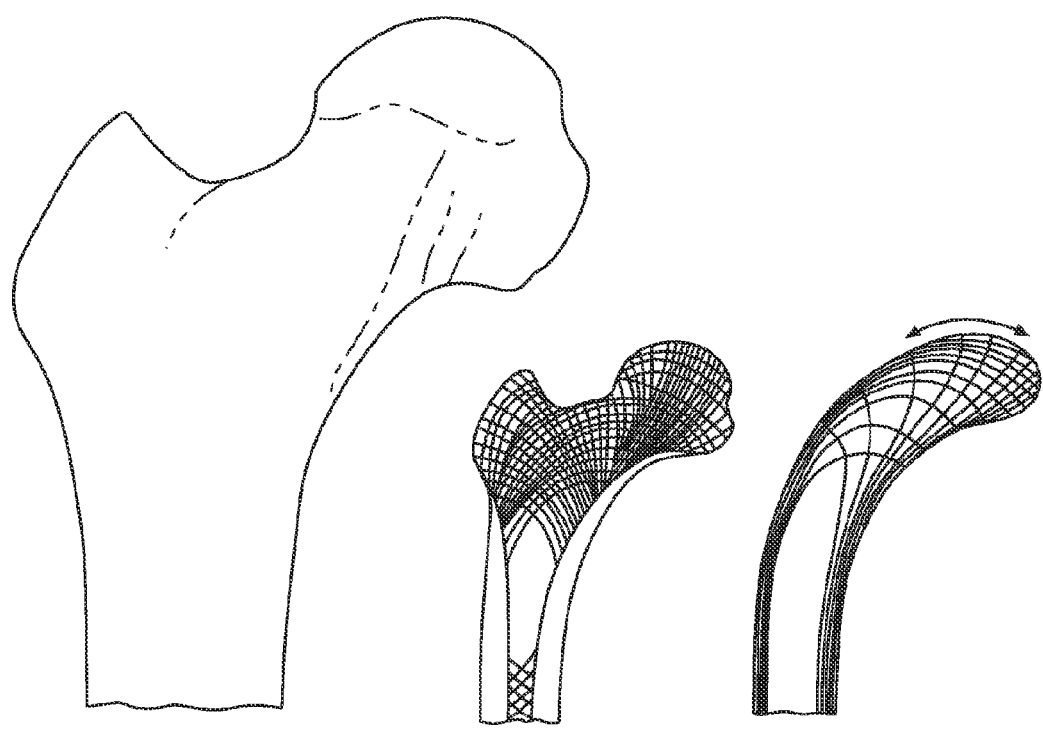
FIGS. 13a and 13b depict how, in exemplary embodiments, a femoral neck scaffold and an intertrochanteric scaffold may be used in conjunction with one another to form an inter-linking scaffold for emulating the anisotropic structural characteristics of the anatomic trabecular structure of the proximal femur.
Figure 13B:
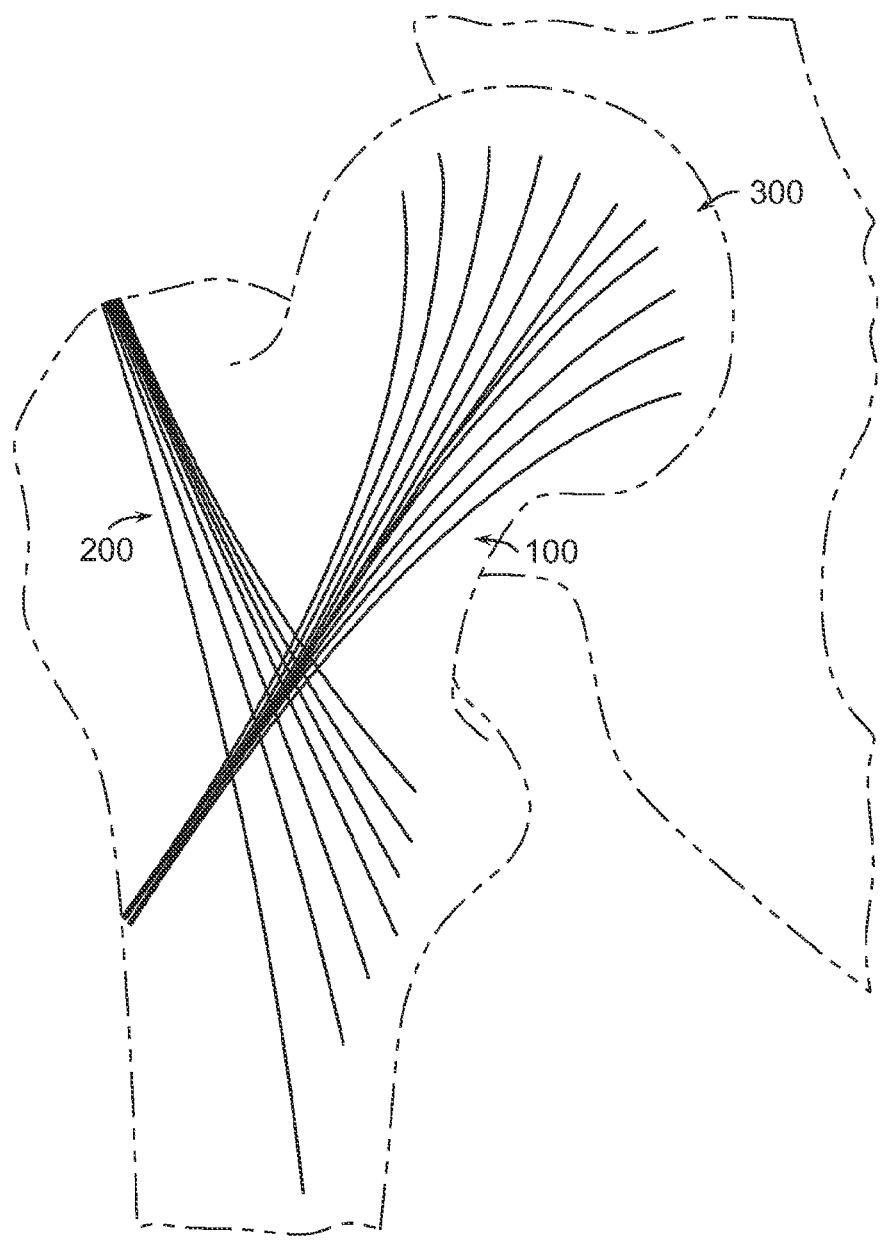

FIGS. 13(*a*) and 13(*b*) depict how, in exemplary embodiments, a femoral neck scaffold 100 (e.g., scaffold 100 of FIGS. 3-7) and an intertrochanteric scaffold 200 (e.g., scaffold 200 of FIGS. 8-12) may be used in conjunction with one another to form an inter-linking scaffold 300 for emulating the anisotropic structural characteristics of the anatomic trabecular structure of the proximal femur (FIG. 13(*a*) depicts the trabecular architecture of the proximal femur characterizing proximal femur anisotropy). More particularly, the femoral neck scaffold 100 and intertrochanteric scaffold 200 may each be implanted and deployed resulting in a crisscrossing of the plurality of struts of the femoral neck scaffold 100 with the plurality of struts of the intertrochanteric scaffold 200. The struts of the interlinking scaffold may then be cross-linked by setting the scaffolds in a composite matrix (e.g., by injecting the composite matrix into the central channels of the femoral neck scaffold 100 and the intertrochanteric scaffold 200 so that it sets around the deployed scaffold 300). As evidenced from comparing FIGS. 13(*a*) and 13(*b*) the interlinking scaffold 300 substantially emulates the trabecular architecture of the proximal femur depicted in FIG. 13(*a*).

Figure 14A:
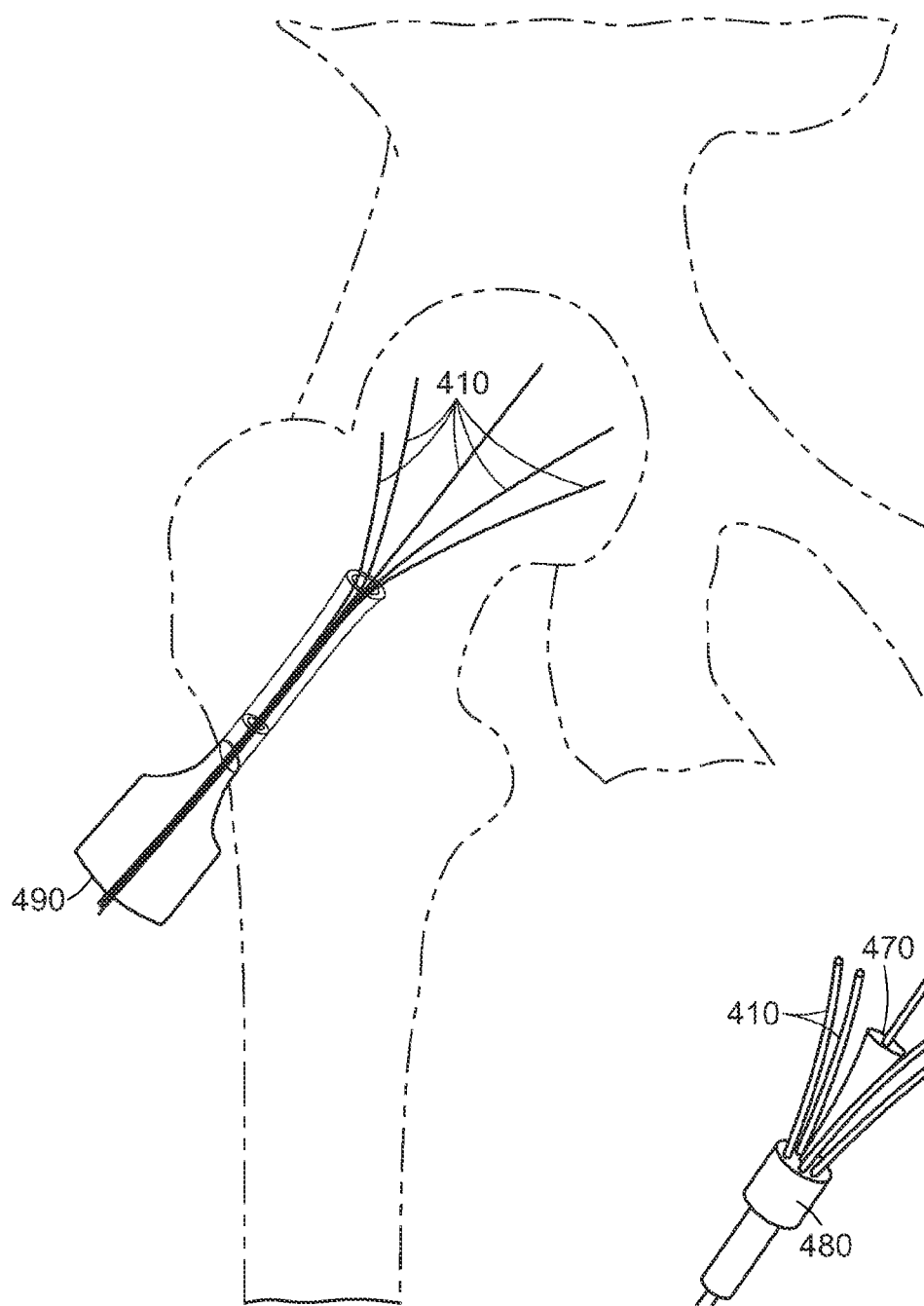
FIGS. 14a and 14b depict exemplary procedures and mechanisms for deploying certain of the expandable scaffolds of the present disclosure.
Figure 14B:
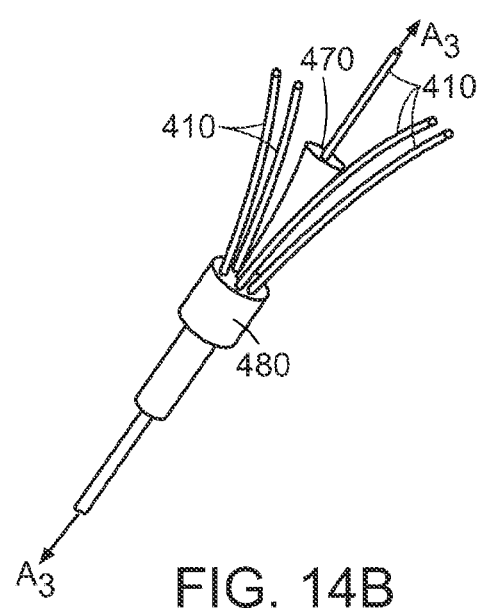
Figure 15:
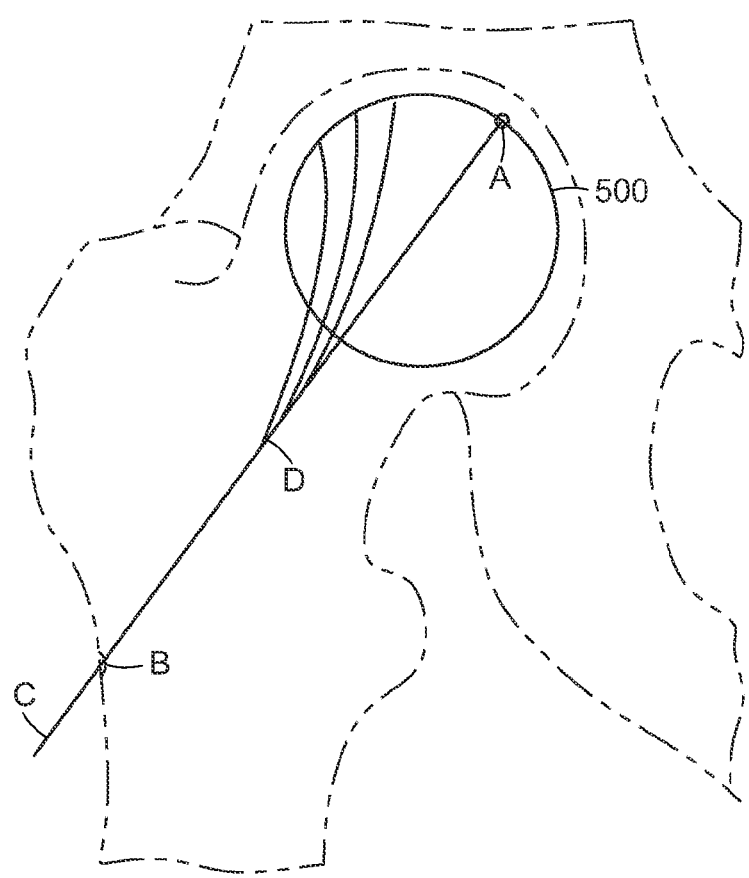
FIG. 15 depicts exemplary procedures and mechanisms for implanting and deploying a femoral neck scaffold.
Figure 16A:
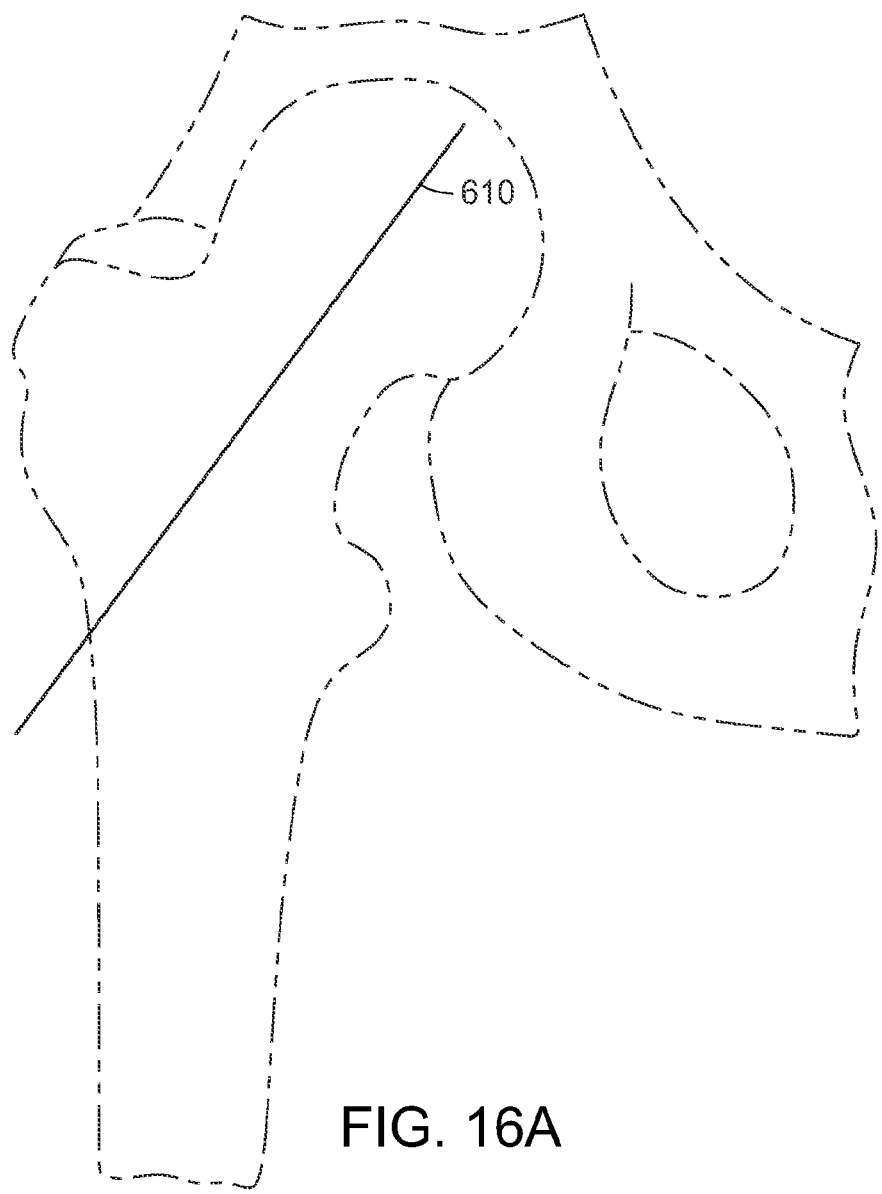
FIG. 16 depicts exemplary procedures and mechanisms for implanting and deploying a femoral neck scaffold.
Figure 16B:
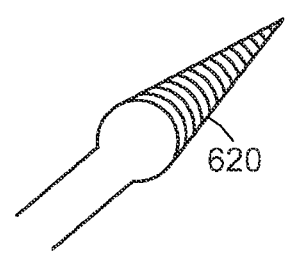
Figure 17A:
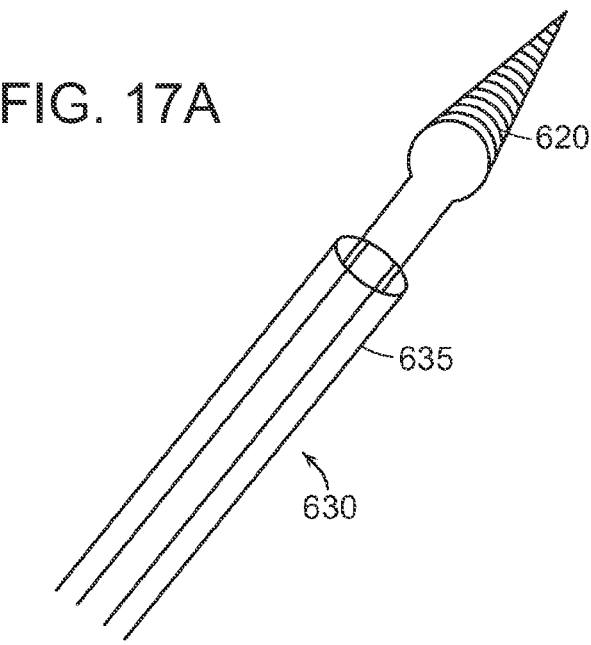
FIG. 17 depicts a guidewire and conical tip used in certain embodiments.
Figure 17B:
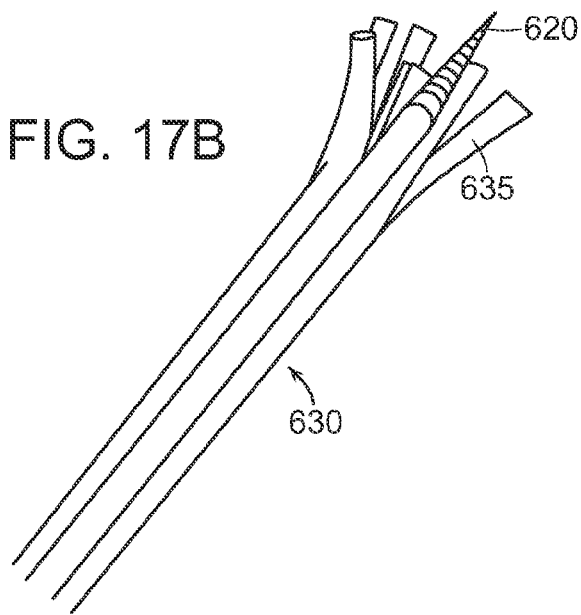
Figure 18:
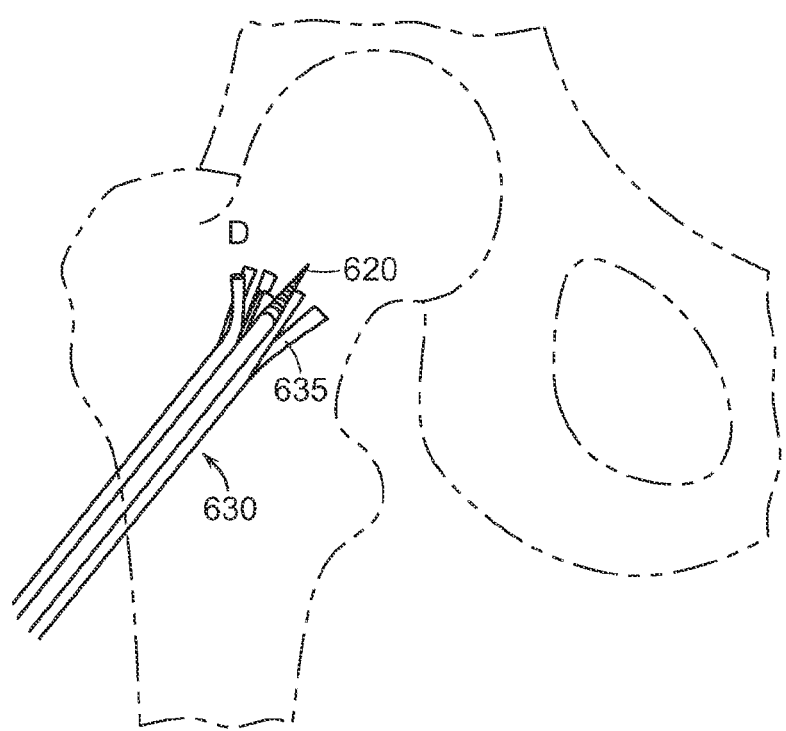
FIG. 18 depicts exemplary procedures and mechanisms for implanting and deploying a femoral neck scaffold using the guidewire and conical tip of FIG. 17.

FIGS. 14(*a*), 14(*b*), 20, 21*a* 21*b* and 22, depict an exemplary procedures and mechanisms for deploying the expandable scaffolds of the present disclosure (e.g., scaffold 100 of FIGS. 3-7 or scaffold 200 of FIGS. 8-12) after implantation. In exemplary embodiments, such as depicted in FIGS. 14(*a*), 14(*b*), 20, 21*a* and 21*b* the deployment mechanism may include one or more guide elements 460, 470, 480 for causing the struts to fan out radially from the central axis and/or for determining a position at which the struts begins to fan out.

For example, as depicted in FIG. 20, the deployment mechanism may include a guide element 460 defining plurality of channels or paths 465 for receiving and threading struts 410 there through, thereby defining a relative positioning, for example, radial and/or angular positioning, and/or curvature of each of the struts 410. In some embodiments, the guide element 460 may define alternative channels or paths 465 for one or more of the struts 410, for example, enabling selection of a desired relative positioning, of the struts 410 and/or enabling selection of a desired curvature of the struts 410. This may be useful in accommodating varying patient physiologies, for example, by allowing for the selection of a desired degree of expansion. In some embodiments, the guide element may first be positioned at an insertion point. The individual struts 410 may then be threaded through to achieve a relative positioning and/or curvature thereof. The guide element 460 may further include one or more apertures for injecting a composite matrix once struts 410 are deployed. Advantageously the guide element 460 may be fixed or removed, post implantation of the scaffold, for example, fixed at or near the point of insertion or removed after the struts 410 are set in the composite matrix.

In other exemplary embodiments, such as depicted in FIGS. 14(*a*), 14(*b*), and 21*a* and 22*b* the deployment mechanism may include a wedge 470 guide element for causing the struts 410 to fan out radially from a central axis A3. As depicted in FIGS. 14(*a*) and 14(*b*) the deployment mechanism may also include a sheath 480 guide element for determining the position at which the struts 410 begin to fan out, for example, proximal to the start of the femoral neck. In some embodiments, the wedge 470 and sheath 480 may be formed as a unitary element (for example, the guide element 460 in FIG. 20 may be adapted to function as both a wedge and a sheath). By adjusting the axial position of the wedge and/or sheath along the central axis A3 the struts can be expanded in a controlled and desired manner (see, e.g., FIGS. 15-18).

Figure 21A:
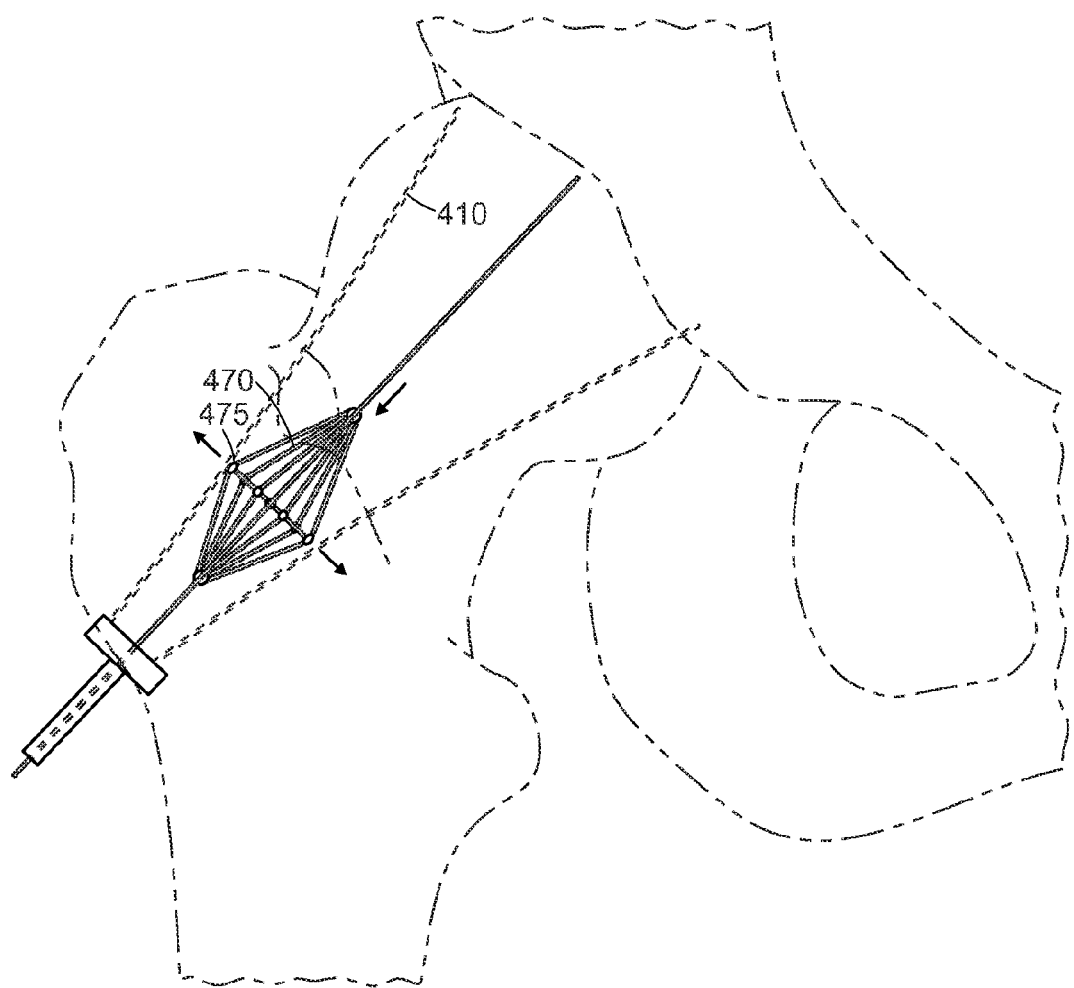
FIGS. 21a and 21b depict further exemplary procedures and mechanisms for deploying certain of the expandable scaffolds of the present disclosure utilizing expandable wedge elements.
Figure 21B:
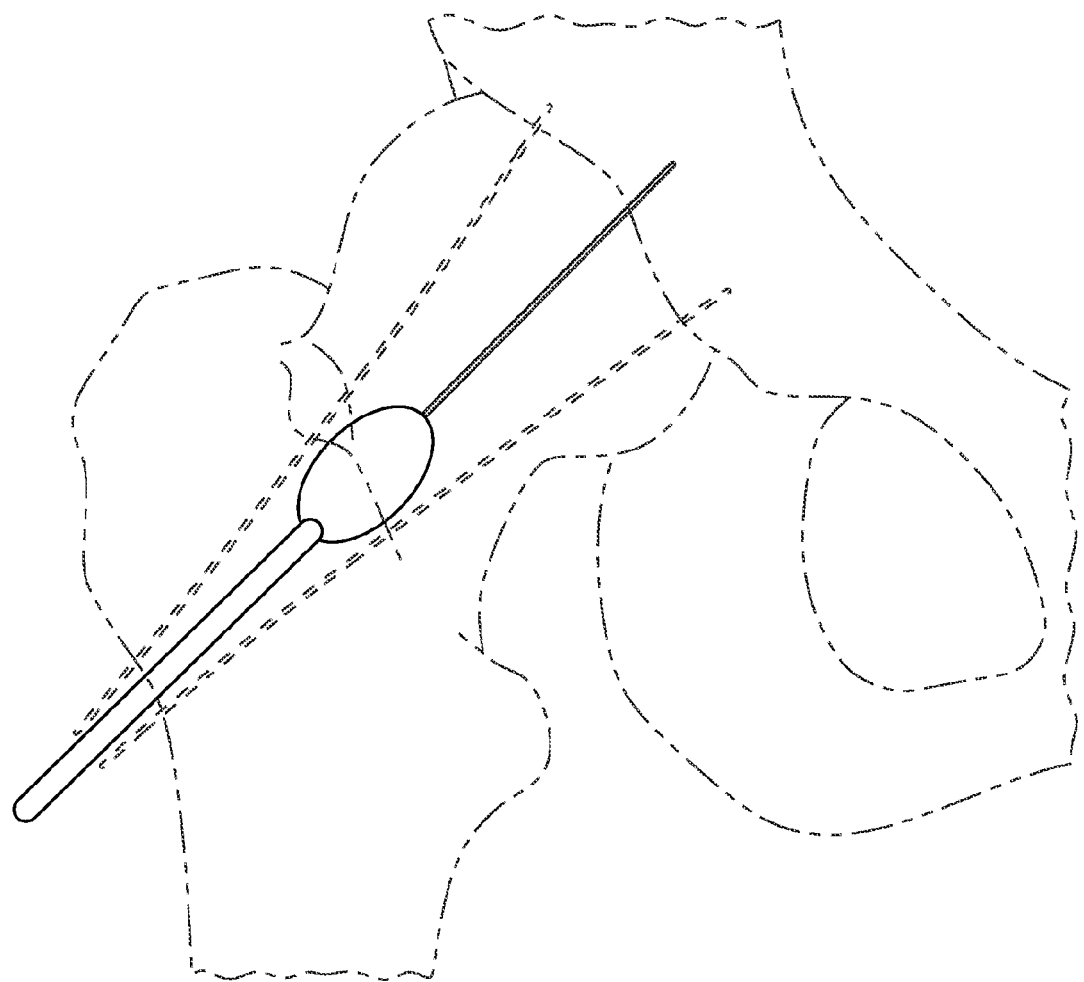

In some embodiments, such as depicted in FIGS. 21*a* and 21*b*), a wedge 470 may be may be deployed from a collapsed state to a radially expanded state. Thus, for example, the wedge may include hinge mechanism 475 which may enable radial expansion of the wedge 470 by axially compressing the wedge 470 (see, e.g., FIG. 21a). Alternatively, the wedge 470 may define an expandable volume, example, for inflation thereof (i.e., the wedge 470 may be a balloon element such as depicted in FIG. 21b). The collapsed state of the wedge may enable insertion/removal thereof via a central channel of the scaffold (e.g., central channel 150 or central channel 250). Once positioned, the wedge 470 may be radially expanded to enable, for example to affect, expansion of the scaffold. The wedge may then be contracted to allow for the removal thereof, e.g., once the struts 410 are properly positioned.

In exemplary embodiments, the deployment mechanism may further include one or more tools, for example, tool 490, for deploying the expandable scaffold. In particular, tool 490 may be adapted to interact with the guide element(s), for example, wedge 470, and/or sheath 480, to selectively deploy or retract the struts 410, as described herein. Other tools may also be used to grasp/manipulate the struts 410.

In some embodiments, the deployment mechanism may be a function of the struts themselves. Thus, as depicted in FIG. 22, in exemplary embodiments, the struts 410 may be formed in part or wholly of a of a shape-memory alloy, shape memory-polymer or other shape-memory material, for example, to facilitate deployment thereof from a collapsed position to an expanded position. In particular, the struts may be configured to curve in a particular direction once the shape-memory is triggered, for example, by an increase in temperature (e.g., based on a body temperature of the patient). Thus, in some embodiments, the struts 410 may be self-expanding upon insertion.

FIGS. 15-18 depict exemplary procedures and mechanisms for implanting and deploying a femoral neck scaffold (e.g., scaffold 100 of FIGS. 3-7), according to the present disclosure. FIGS. 15-18 are exemplary. As a first step for implanting the femoral neck scaffold, C-arm can be used to visualize the uninjured proximal femur (anteroposterior view) in a supine patient with the leg extended. A traction table may be utilized with position analogous as would be done for percutaneous pinning. Next, an insertion guide template (see FIG. 15), can be overplayed over the patient's hip to the planned position of the scaffold, so that the circle portion 500 of the insertion guide overlies the profile of the femoral head in a concentric manner, and the axial tip (Point A) is in the subchondral position at the apex of the femoral head. The guide's vertical marks can be used to match the lateral cortex of the femur to assure an approximate 135 degrees direction along the femoral neck (relative to the femoral cavity). This can be the location (Point B) where the scaffold will enter the lateral cortex. The patient's skin can be marked where the lateral extension of the insertion template guide intersects the skin (Point C). This is the location where a 2 cm incision is made for insertion of the scaffold. Next, the insertion guide template can be used to estimate the equatorial location in the femoral head, where one would like to offer subchondral support. Thus, the guide can be to visualize along the femoral neck axis, the position where the divergence (fanning out) of the struts will occur (Point D in FIG. 15). In exemplary embodiments, the divergence point is preferably as lateral as possible while still allowing for the distal ends of the struts to provide subchondral support close to the mid equatorial location of the femoral head (see, e.g., FIG. 13(b)).

Next, using a combination of anteroposterior and lateral views, and starting at an entry point on the lateral cortex of the femur below the lesser trochanter where the lateral extension arm of the insertion guide template intersects the lateral cortex of the femur, a 2 mm diameter central guide wire 610 with a 3 mm diameter conical tip 620 (see FIG. 16) is inserted into the femoral head, so that tip to apex distance is optimized. In exemplary embodiments, the entry angle relative to the femoral shaft for this insertion is in the order of 135 degrees. The tip of the 2 mm guidewire 610 with the 3 mm conical tip 620 should be advanced to a subchondral position in the apex of the femoral head. From there, the intraosseous length of the 2 mm guidewire 610 with the 3 mm conical tip 620 can be measured using the depth gage. This measurement can be used to determine the length of the struts for the scaffold to be inserted.

Next, the lateral cortex of the femur is over drilled with the 5 mm diameter cannulated drill. A 10 mm protection sleeve may be inserted over the guide wire through the soft tissues until it reaches the lateral cortex of the bone. It should fit loosely over the wire. Next a 3 mm plastic sleeve 630 with a precut distal end 635 for flaring is inserted over the 2 mm guidewire 610 (See FIGS. 17 and 18). As noted above, the insertion guide template can be used to estimate the desired point of initiation of divergence of the struts (Point D). The plastic sleeve 630 is advanced to this point. Then holding the plastic sleeve 630 in place, the 2 mm guidewire 610 with the 3 mm conical tip 620 can be extracted until the 3 mm conical tip 620 comes in contact with the precut end 635 of the plastic sleeve 630 and flares it open (See, in particular FIG. 17(b)). Once the 3 mm plastic sleeve 630 is flared, it will act as a wedge for the struts of the scaffold which is then inserted over the 3 mm plastic sleeve 630. In particular, the scaffold may include a 3 mm central channel that will slide over the 3 mm plastic sleeve 630. As the scaffold is advanced, the struts reach the flared end 635 of the 3 mm plastic sleeve 630 and start diverging towards the equatorial area of the femoral head as they are advanced. In exemplary embodiments, prior to insertion, the struts are trimmed to the length measured initially over the 2 mm guidewire 610 minus an offset, e.g., of approximately 20 mm. If the struts are not properly shortened the threaded proximal end of the scaffold may protrude more than 5 mm and cause bursal irritation. Once the scaffold is in position, the cannulated plastic sleeve 630 can be removed followed by the 2 mm guidewire 610 with the 3 mm conical tip 620.

Similar procedures and mechanisms may be used for implanting and deploying a intertrochanteric scaffold (e.g., scaffold 200 of FIGS. 8-12), alone or in conjunction with a femoral neck scaffold. In general, where the intertrochanteric scaffold is used in conjunction with the femoral neck scaffold, the intertrochanteric scaffold should only be inserted after the femoral neck scaffold is in-situ. This is because there is greater difficulty inserting the femoral neck scaffold if the intertrochanteric scaffold is inserted first. Typically, no insertion template is required for inserting the intertrochanteric scaffold.

The entry point for the intertrochanteric scaffold is 1 cm lateral to the trochanteric apex. A 2 mm guidewire with a 3 mm conical tip similar to that described with respect to FIGS. 16-18) can be inserted so that the tip is aimed at the distal margin of the lesser trochanter. The intraosseous length over the 2 mm guidewire can be measured using the depth gage. This can be used to determine the length of the struts for the intertrochanteric scaffold to be inserted. Please note the measured length measured reflects the shorter struts of the intertrochanteric scaffold that terminate proximate to the lesser trochanteric area. The longer branches of the intertrochanteric scaffold will extend further distally into the canal (see FIG. 13(b)).

Next the entry point is over drilled with a 5 mm cannulated drill. In exemplary embodiments, a 10 mm protection sleeve can be placed over the guide wire through the soft tissues until it reaches the cortex of the bone. It should fit loosely over the wire. As was the case with the femoral neck scaffold, a cannulated 3 mm plastic sleeve with a precut distal end for flaring can be inserted over the 2 mm guidewire and inserted to the desired point of initiation of divergence of the struts for the intertrochanteric scaffold. In exemplary embodiments, the desired point of initiation of divergence of the struts for the intertrochanteric scaffold is 2 cm after entry. Next, while holding the plastic sleeve in place, the 2 mm guidewire can be extracted until the 3 mm conical tip contacts the precut end and flares it open. As was for the femoral neck scaffold, the purpose of this flare is to act as wedge and initiate the divergence of the struts of the intertrochanteric scaffold which is inserted over the 3 mm cannulated sleeve. The intertrochanteric scaffold may define a 3 mm central channel that will slide over the 3 mm cannulated sleeve. As the intertrochanteric scaffold is advanced, the struts reach the flared end of the 3 cannulated sleeve and start diverging. The intertrochanteric scaffold should be inserted with the longer branches in the caudal position relative to the entry point so that when they diverge they advance into the femoral shaft while the shorter branches are directed towards the intertrochanteric area. In exemplary embodiments, before insertion the struts directed towards the intertrochanteric area can be trimmed to the length measured initially over the 2 mm guidewire minus an offset, e.g., minus 20 mm. If the struts are not properly shortened the threaded proximal end of the intertrochanteric scaffold may protrude more than 5 mm and cause bursal irritation. Once the intertrochanteric scaffold is in position, the cannulated plastic sleeve can be removed followed by the 2 mm guidewire with the 3 mm conical tip.

Figure 19:
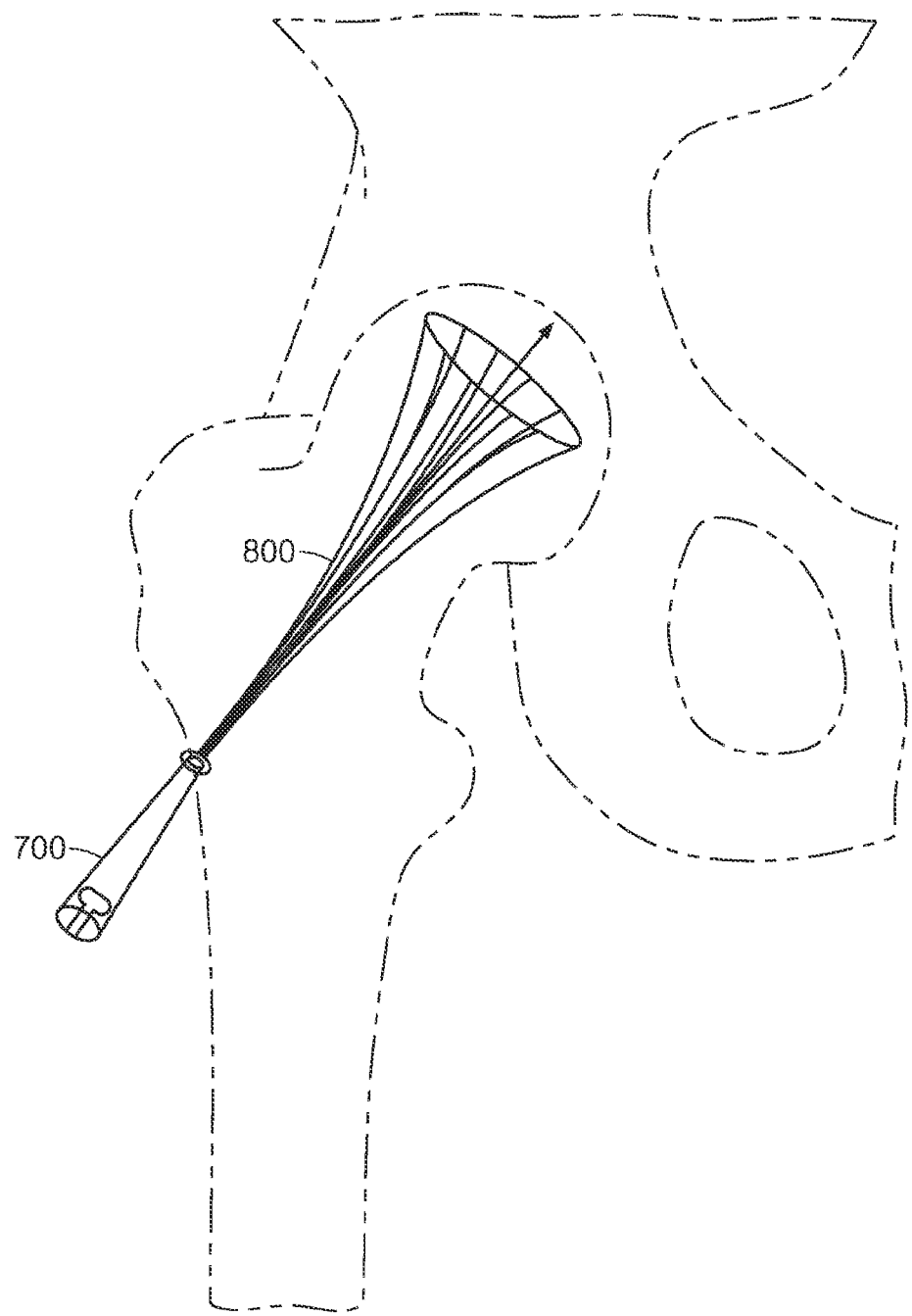
FIG. 19 depicts exemplary procedures and mechanisms for implanting and deploying a femoral neck scaffold.

Referring to FIG. 19, once a scaffold 800 (e.g., scaffold 100 of FIG. 3-7 or scaffold 200 of FIGS. 8-12) is implanted and deployed it may be set in a polymer matrix, e.g., by injecting the polymer matrix into the central channel of the scaffold 800. In exemplary embodiments an injection tool may interface with the proximal end of the scaffold, e.g., with the threaded portion of the scaffold, to enable injection of the polymer matrix.

All values, measures and dimensions referenced herein are approximate. It is further noted that all values, measure or dimensions referenced herein are exemplary and are not limiting with respect to any of the embodiments described herein.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

The invention claimed is:

1. A system for improving the structural integrity of at least a portion of a bone, the system comprising:
a first plurality of flexible struts configured to be inserted into the bone along a first axis, wherein the distal ends of the first plurality of flexible struts transition from the collapsed state to a radially expanded state when deployed such that the distal ends individually fan out radially about the first axis and extend distal to a guide element wherein channels of the guide element define a divergence of each strut relative to the first axis during insertion into the bone to establish directional anisotropy along the first axis within the bone; and
a filler material that is injectable about at least a portion of the first plurality of radially expanded struts located distally in relation to the guide element.

2. The system of claim 1, wherein the first plurality of struts each have substantially a same length.

3. The system of claim 1, wherein the first plurality of struts are configured to be positioned within a femur bone at a location substantially opposite a femoral head of the femur bone, such that the first axis substantially passes into the femoral head and wherein at least some of the first plurality of struts are configured to pass through the femoral neck and enter the femoral head.

4. The system of claim 1, wherein at least two of the first plurality of struts have different lengths.

5. The system of claim 1, wherein the first plurality of struts are configured for insertion into a greater trochanter of a femur bone and the first axis extends generally from the greater trochanter to a lesser trochanter of the femur bone.

6. The system of claim 5, wherein, when the first plurality of struts is in the expanded state, a first set of one or more of the first plurality of struts are configured for positioning cephally for termination at the lesser trochanter and a second set of the one or more of the first plurality of struts are configured for positioning caudally for termination at the subtrochanteric area in the femoral canal, wherein the first set of struts is shorter than the second set of struts.

7. The system of claim 1, further comprising a second plurality of struts for insertion into the bone along a second axis different from the first axis, wherein the second plurality of struts are expandable substantially radially about the second axis to establish directional anisotropy along the second axis within the bone.

8. The system of claim 7, wherein the first and second pluralities of struts are configured to crisscross to form an inter-linking scaffold in the bone.

9. The system of claim 7, wherein the first plurality of struts each have a substantially same length and wherein at least two of the second plurality of struts have different lengths.

10. The system of claim 7, wherein the first plurality of struts are configured for insertion into a femur bone at a location substantially opposite a femoral head of the femur bone, such that the first axis substantially passes into the femoral head and at least some of the first plurality of struts are configured to pass through the femoral neck and enter the femoral head and wherein the second plurality of struts are configured for insertion into a greater trochanter of the femur bone and the second axis extends generally from the greater trochanter to a lesser trochanter of the femur bone.

11. The system of claim 10, wherein the at least some of the first plurality of struts are configured such that, when the first plurality of struts is in the expanded state, a termination of a distal end of the at least some of the first plurality of struts is adapted to be around the equatorial femoral head.

12. The system of claim 10, wherein, when the second plurality of struts is in an expanded state, a first set of one or more of the second plurality of struts are configured for positioning cephally for termination at the lesser trochanter and a second set of the one or more of the second plurality of struts are configured for positioning caudally for termination at the subtrochanteric area in the femoral canal, wherein the first set of struts is shorter than the second set of struts.

13. The system of claim 1, wherein the guide element is operatively associated with the first plurality of flexible struts for at least one of (i) guiding the first plurality of struts to fan out or (ii) defining a position at which the first plurality of struts begins to fan out.

14. The system of claim 13, wherein channels of the guide element thread the first plurality of struts, whereby a relative positioning of each of the threaded struts is determined.

15. The system of claim 13, wherein the guide element comprises a wedge element such that the first plurality of struts fans out radially.

16. The system of claim 15, wherein the wedge element defines an expandable volume and is adapted for deployment from a collapsed state to a radially expanded state and wherein the collapsed state of the wedge element enables insertion or removal thereof through a central channel defined by the first plurality of struts.

17. The system of claim 16, wherein the wedge element includes a hinge mechanism which enables radial expansion of the wedge element when the wedge element is axially compressed.

18. The system of claim 1, wherein the first plurality of struts is formed at least in part of a shape-memory material having shape-memory, whereby the struts are configured to curve in a particular direction in response to the shape-memory.

19. The system of claim 1, wherein the first plurality of struts are configured to be substantially intraosseous and include at least 8 struts.

20. The system of claim 1, wherein the first plurality of struts are arranged in a circumferential arrangement to define an overall diameter of approximately 5 mm or less and the circumferential arrangement defines a central channel of approximately 3 mm.

21. The system of claim 1, wherein the filler material comprises a composite matrix.

22. The system of claim 1, wherein the guide element defines a divergence point from which the distal ends expand radially during movement into a trabecular structure of the bone to emulate anisotropic structural characteristics of the trabecular structure of the bone, the distal ends of the first plurality of flexible struts becoming fixed relative to one another upon setting of the filler material.

23. The system of claim 1 wherein the guide element is removable from the first plurality of flexible struts upon positioning of the distal ends in the bone.

24. An implanted system for improving the structural integrity of at least a portion of a bone, the system comprising a first plurality of flexible struts configured to be inserted into the bone along a first axis and set in a filler material at a position distal to a guide element upon insertion into the bone, wherein distal ends of the first plurality of struts separately fan out radially from the first axis at a distal end of the first plurality of the struts and extend distal to the guide element such that the distal ends have differing radii relative to the first axis, the first plurality of struts thereby establishing directional anisotropy along the first axis within the bone.

25. The system of claim 24, wherein the first plurality of struts each have a substantially same length.

26. The system of claim 24, wherein the first plurality of struts are characterized by a plurality of different lengths.

27. The system of claim 24, wherein the first plurality of struts are configured to be inserted into a femur bone at a location substantially opposite a femoral head of the femur bone, such that the first axis substantially passes through the femoral head.

28. The system of claim 24, further comprising a second plurality of struts configured to be inserted into the bone along a second axis different than the first axis and set in a filler material, wherein the second plurality of struts fans out radially from the second axis at a distal end of the second plurality of the struts, the second plurality of struts establishing directional anisotropy along the second axis within the bone.

29. The system of claim 28, wherein the first and second pluralities of struts crisscross to form an inter-linking scaffold.

30. The system of claim 29, wherein the filler material cross-links the first and second pluralities of struts.

31. A system for improving the structural integrity of at least a portion of a bone, the system comprising:
 a first plurality of flexible struts that are free at their distal ends when in a collapsed state and that are configured to be inserted into the bone along a first axis, wherein the distal ends of the first plurality of flexible struts transition from the collapsed state to a radially expanded state such that the distal ends individually fan out radially about the first axis during insertion into the bone to establish directional anisotropy along the first axis within the bone;
 a guide element positionable at an insertion point of the bone and comprising a channel corresponding to each of the first plurality of flexible struts and through which the strut is threaded to define a radial position of the distal end of the strut; and
 a filler material that is injectable about at least a portion of the first plurality of radially expanded struts;
 wherein the distal ends of the first plurality of flexible struts extend distally in relation to the guide element and the filler material covers a portion of the first plurality of radially expanded struts that is located distally in relation to the guide element, and
 wherein the guide element defines a divergence of each strut relative to the first axis.

32. The system of claim 31, wherein the guide element defines a divergence point from which the distal ends expand radially during movement into a trabecular structure of the bone to emulate anisotropic structural characteristics of the trabecular structure of the bone, the distal ends of the flexible struts becoming fixed relative to one another upon setting of the filler material.

33. The system of claim 31, wherein the guide element is removable from the first plurality of flexible struts upon positioning of the distal ends in the bone.

34. The system of claim 31, wherein the first plurality of flexible struts are configured to be substantially intraosseous and include at least 8 struts.

35. The system of claim 31, wherein the filler material comprises a composite matrix.

* * * * *